(12) United States Patent
Friedman et al.

(10) Patent No.: US 12,083,130 B2
(45) Date of Patent: Sep. 10, 2024

(54) COMBINATION HORMONE FORMULATIONS AND THERAPIES

(71) Applicant: Caren Pharmaceuticals, Inc., Skokie, IL (US)

(72) Inventors: Arnold Edward Friedman, Skokie, IL (US); Rebecca L. Glaser, Skokie, IL (US)

(73) Assignee: Caren Pharmaceuticals, Inc., Wilmington, DE (US)

( * ) Notice: Subject to any disclaimer, the term of this patent is extended or adjusted under 35 U.S.C. 154(b) by 0 days.

(21) Appl. No.: 17/255,927

(22) PCT Filed: Oct. 1, 2020

(86) PCT No.: PCT/US2020/053809
§ 371 (c)(1),
(2) Date: Dec. 23, 2020

(87) PCT Pub. No.: WO2021/067600
PCT Pub. Date: Apr. 8, 2021

(65) Prior Publication Data
US 2022/0305030 A1 Sep. 29, 2022

Related U.S. Application Data

(60) Provisional application No. 62/910,227, filed on Oct. 3, 2019, provisional application No. 62/910,225, filed on Oct. 3, 2019.

(51) Int. Cl.
*A61K 31/57* (2006.01)
*A61K 31/4196* (2006.01)
*A61K 31/473* (2006.01)
*A61K 31/568* (2006.01)
*A61K 31/573* (2006.01)
*A61K 31/593* (2006.01)
*A61P 25/28* (2006.01)

(52) U.S. Cl.
CPC .......... *A61K 31/57* (2013.01); *A61K 31/4196* (2013.01); *A61K 31/473* (2013.01); *A61K 31/568* (2013.01); *A61K 31/573* (2013.01); *A61K 31/593* (2013.01); *A61P 25/28* (2018.01)

(58) Field of Classification Search
CPC .. A61K 31/57; A61K 31/4196; A61K 31/586; A61K 31/573; A61K 31/568
See application file for complete search history.

(56) References Cited

U.S. PATENT DOCUMENTS

| | | | |
|---|---|---|---|
| 8,148,546 B2 | 4/2012 | Schuster et al. | |
| 10,071,104 B2 | 9/2018 | Glaser | |
| 2005/0032762 A1* | 2/2005 | Hubler | A61K 47/44 424/731 |
| 2007/0027123 A1* | 2/2007 | Labrie | A61K 31/66 514/170 |
| 2009/0170783 A1 | 7/2009 | Schuster et al. | |
| 2010/0144687 A1* | 6/2010 | Glaser | A61P 5/24 514/171 |
| 2016/0051565 A1* | 2/2016 | Wang | A61K 31/366 514/171 |
| 2017/0035783 A1 | 2/2017 | Schaller | |

FOREIGN PATENT DOCUMENTS

WO WO 2010/0653858 A1 6/2010
WO WO 2016/061615 * 4/2016 ......... A61K 31/5685

OTHER PUBLICATIONS

Montgomery et al. "Glucocorticoids and prostate cancer treatment : friend or foe?" Asian J. Andrology, 2014, 16, pp. 354-358 (Year: 2014).*
PCT International Search Report and Written Opinion, dated Feb. 25, 2021, 13 pages.
Wahjoepramono et al., "The Effects of Testosterone Supplemental on Cognitive Functioning in Older Men", CNS & Neurological Disorders—Drug Targets, 2016, 15, 337-343.
Wikipedia, "Estriol" Mar. 3, 2018 (Mar. 3, 2018 ), retrieved on Dec. 1, 2020 from https://en.wikipedia.org/w/index.php?title=Estriol &oldid=828573003; entire document, especially p. 1 para 1.
Abbott et al., "Serum estradiol and risk of stroke in elderly men", Neurology, vol. 68, dated Feb. 20, 2007, pp. 563-568.
Abramov et al., "Amyloid-β as a positive endogenous regulator of release probability at hippocampal synapses", Nature Neuroscience, vol. 12, No. 12, dated Dec. 2009, pp. 1567-1576.
Amtul et al., "Neuroprotective Mechanism Conferred by 17Beta-Estradiol on the Biochemical Basis of Alzheimer's", Neuroscience, vol. 169, No. 2, dated Aug. 25, 2010, pp. 781-786.
Barrett-Connor et al., "The Association of Testosterone Levels with Overall Sleep Quality, Sleep Architecture, and Sleep-Disordered Breathing, The Journal of Clinical Endocrinology & Metabolism", vol. 93, No. 7, dated Apr. 15, 2008, pp. 2602-2609.
Basaria et al., "Adverse Events Associated with Testosterone Administration", The New England Journal of Medicine, vol. 363, No. 2, dated Jul. 8, 2010, pp. 109-122.
Bassil et al., "The benefits and risks of testosterone replacement therapy: a review", Therapeutics and Clinical Risk Management, vol. 5, No. 3, dated Jun. 22, 2009, pp. 427-448.
Bishop et al., "Estradiol Enhances Brain Glucose Uptake in Ovariectomized Rats", Brain Research Bulletin, vol. 36, No. 3, dated 1995, pp. 315-320.

(Continued)

*Primary Examiner* — Craig D Ricci
(74) *Attorney, Agent, or Firm* — Knobbe, Martens, Olson & Bear, LLP

(57) ABSTRACT

Disclosed herein are compositions and methods useful for the treatment or amelioration of various diseases, disorders, or conditions. Some aspects pertain to a composition comprising a testosterone source, an aromatase inhibitor, and an estriol source. Also presented herein is the surprising discovery that exposing a subject to the compositions disclosed herein can increase a subject's longevity, survival time, life span, and health span, as well as treat Alzheimer's disease.

20 Claims, 2 Drawing Sheets

(56) References Cited

OTHER PUBLICATIONS

Bove et al., "Low testosterone is associated with disability in men with multiple sclerosis", Mult Scler, vol. 20, No. 12, dated Oct. 2014, pp. 1584-1592.
Branning, "Study finds testosterone therapy can lead to remission in men with Type 2 diabetes", UBNow, dated Aug. 5, 2020, https://www.buffalo.edu in 3 pages.
Carroll et al., "Progesterone and Estrogen Regulate Alzheimer-Like Neuropathology in Female 3xTg-AD Mice", The Journal of Neuroscience, vol. 27, No. 48, dated Nov. 28, 2007, p. 13357-13365.
Carroll et al., "Continuous and Cyclic Progesterone Differentially Interact with Estradiol in the Regulation of Alzheimer-Like Pathology in Female 3xTransgenic-Alzheimer's Disease Mice", Endocrinology, vol. 151, No. 6, dated Jun. 2010, pp. 2713-2722.
Chitnis, "The role of testosterone in MS risk and course", Multiple Sclerosis Journal, vol. 24, dated 2018, pp. 36-41.
Cole et al., "The Alzheimer's disease β-secretase enzyme, BACE I", Molecular Neurodegeneration, vol. 2, No. 22, dated Nov. 15, 2007 in 25 pages.
Driscoll et al., "Testosterone and Cognition in Normal Aging and Alzheimer's Disease: An Update", Current Alzheimer Research, vol. 4, No. 1, dated 2007, pp. 33-45.
Ebinger et al., "Is there a neuroendocrinological rationale for testosterone as a therapeutic option in depression?" Journal of Psychopharmacology, vol. 23, No. 7, dated Sep. 2009, pp. 841-853.
Farnsworth, "Estrogen in the Etiopathogenesis of BPH", The Prostate, vol. 41, No. 4, dated Dec. 1999, pp. 263-274.
Felicetta, "Will Testosterone Replacement Therapy Kill Your Patient?", Federal Practitioner, vol. 3, No. 11, dated Nov. 2014 in 2 pages.
Finkle et al., "Increased Risk of Non-Fatal Myocardial Infarction Following Testosterone Therapy Prescription in Men", PLoS One, vol. 9, dated Jan. 2014 in 7 pages.
Friedman, "Re: Abraham Morgentaler, Abdulmaged M. Traish. Shifting the Paradigm of Testosterone and Prostate Cancer: The Saturation Model and the Limits of Androgen-Dependent Growth", Letter to the editor-European Association of Urology, 2009, 1 page.
Friedman, "Response-Re: Abraham Morgentaler, Abdulmaged M. Traish. Shifting the Paradigm of Testosterone and Prostate Cancer: The Saturation Model and the Limits of Androgen-Dependent Growth", Letter to the editor-European Association of Urology, 2009, 1 page.
Friedman, "Aromatase Explains Why Testosterone Increases Breast Cancer Rate", Letter to the editor—American Association for Cancer Research, 2009, 1 page.
Friedman, "Can a single model explain both breast cancer and prostate cancer?", Theoretical Biology and Medical Modelling, 2007, 4:28, 13 pages.
Friedman, "The Strengths and Weaknesses of Bipolar Androgen Therapy", https://www.researchgate.net/publication/362276475, 2022, 6 pages.
Friedman, "The Estradiol-Dihydrotestosterone model of prostate cancer", Theoretical Biology and Medical Modelling, 2005, 4 pages.
Friedman, "Global Consensus Position Statement on the Use of Testosterone Therapy for Women", Letter to the editor—J Clin Endocrinol Metab, Jun. 2020, 105(6), 2 pages.
Friedman, "Regarding Prostatic hormonal carcinogenesis is meditated by in situ estrogen production and estrogen receptor alpha signaling", Letter to the editor—The FASEB Journal, 2009, vol. 23, 3 pages.
Friedman, "Response-Regarding Prostatic hormonal carcinogenesis is meditated by in situ estrogen production and estrogen receptor alpha signaling", Letter to the editor—The FASEB Journal, 2009, vol. 23, 3 pages.
Friedman, "Hormones are the Answer to Alzheimer's Disease", dated 2018 in 16 pages.
Friedman, "The Relationship Between Testosterone, Estradiol, and Prostate Cancer", https://www.researchgate.net/publication/305122202, 2016, 14 pages.
Friedman et al., "How You and Your Doctor Can Fight Breast Cancer Prostate Cancer and Alzheimer's", The New Testosterone Treatment, 2013, pp. 1-200, part 1.
Friedman et al., "How You and Your Doctor Can Fight Breast Cancer Prostate Cancer and Alzheimer's", The New Testosterone Treatment, 2013, pp. 201-400, part 2.
Gabel et al., "Estrogen receptor beta mediates gender differences in ischemia/reperfusion injury", Journal of Molecular and Cellular Cardiology, vol. 38, dated 2005, pp. 289-297.
Glaser et al., "Testosterone implants in women: Pharmacological dosing for a physiologic effect", Maturitas, vol. 74, No. 2, dated Feb. 2013, pp. 179-184.
Glaser et al., "Reduced breast cancer incidence in women treated with subcutaneous testosterone, or testosterone with anastrozole: A prospective, observational study", Maturitas, vol. 76, dated 2013, pp. 342-349.
Gong et al., "Hyperphosphorylation of Microtubule-Associated Protein Tau: A Promising Therapeutic Target for Alzheimer Disease", Curr Med Chem, vol. 15, No. 23, dated 2008, pp. 2321-2328.
Gong et al., "Impaired brain glucose metabolism leads to Alzheimer neurofibrillary degeneration through a decrease in tau O-GlcNAcylation", Journal of Alzheimer's Disease, vol. 9, dated Mar. 2006 in 12 pages.
Gouras et al., "Testosterone reduces neuronal secretion of Alzheimer's β-amyloid peptides", PNAS, vol. 97, No. 3, dated Feb. 1, 2000, pp. 1202-1205.
Gu et al., "Alzheimer's Aβ42 and Aβ40 peptides form interlaced amyloid fibrils", J Neurochem, vol. 126, No. 3, dated Aug. 2013, pp. 305-311.
Haider et al., "Incidence and severity of prostate cancer (PCa) in 792 hypogonadal men with and without long-term testosterone therapy (TTh): Results from a controlled registry study." Journal of Clinical Oncology, vol. 36, dated Feb. 2018 in 5 pages.
Haider et al., "Remission of type 2 diabetes following long-term treatment with injectable testosterone undecanoate in patients with hypogonadism and type 2 diabetes: 11-year data from a real-world registry study", Diabetes Obes Metab, vol. 22, No. 11, dated Nov. 2020, pp. 2055-2068.
Hurn et al., "Postischemic Cerebral Blood Flow Recovery in the Female: Effect of 17β-Estradiol", Journal of Cerebral Blood Flow and Metabolism, vol. 15, dated 1995, pp. 666-672.
Imamov et al., "Estrogen receptor β regulates epithelial cellular differentiation in the mouse ventral prostate", PNAS, vol. 101, No. 25, dated Jun. 22, 2004, pp. 9375-9380.
Jankowska et al., "Circulating Estradiol and Mortality in Men With Systolic Chronic Heart Failure", JAMA, vol. 301, No. 18, dated May 13, 2009, pp. 1892-1901.
Jayachandran et al., "Loss of estrogen receptor β decreases mitochondrial energetic potential and increases thrombogenicity of platelets in aged female mice", Age, vol. 32, dated 2010, pp. 109-121.
Jones et al., "Randomized controlled trials—mechanistic studies of testosterone and the cardiovascular system", Asian Journal of Andrology, vol. 20, dated 2018, pp. 120-130.
Koudinov et al., "Alzheimer's amyloid-beta (Aβ) is an essential synaptic protein, not neurotoxic junk", Acta Neurobiologiae Experimentalis, vol. 64, dated 2004, pp. 71-79.
Kanemitsu et al., "Human neprilysin is capable of degrading amyloid β peptide not only in the monomeric form but also the pathological oligomeric form", Neuroscience Letters, dated 2003, pp. 113-116.
Lam et al., "Durable Response of Enzalutamide-resistant Prostate Cancer to Supraphysiological Testosterone Is Associated with a Multifaceted Growth Suppression and Impaired DNA Damage Response Transcriptomic Program in Patient-derived Xenografts", Eur Urol., vol. 77, No. 2, dated Feb. 2020, pp. 144-155.
Lannert et al., "Effects of Estradiol (-17β) on learning, memory and cerebral energy metabolism in male rats after intracerebroventricular administration of streptozotocin", J Neural Transm, vol. 105, dated 1998, pp. 1045-1063.
Liu et al., "The Short-Term Effects of High-Dose Testosterone on Sleep, Breathing, and Function in Older Men", The Journal of Clinical Endocrinology & Metabolism, vol. 88, No. 8, dated 2003, pp. 3605-3613.

(56) References Cited

OTHER PUBLICATIONS

Lu et al., "Effects of Testosterone on Cognition and Mood in Male Patients With Mild Alzheimer Disease and Healthy Elderly Men", Arch Neurol., vol. 63, dated 2006, pp. 177-185.

McAllister et al., "Genetic Targeting Aromatase in Male Amyloid Precursor Protein Transgenic Mice Down-Regulates β-Secretase (BACE1) and Prevents Alzheimer-Like Pathology and Cognitive Impairment", J Neurosci, vol. 30, No. 21, dated May 26, 2010, pp. 7326-7334.

Michaud et al., "Testosterone and prostate cancer: an evidence-based review of pathogenesis and oncologic risk", Therapeutic Advances in Urology, vol. 7, No. 6, dated 2015, pp. 378-387.

Miller et al., "Peptide Compositions of the Cerebrovascular and Senile Plaque Core Amyloid Deposits of Alzheimer's Disease", Archives of Biochemistry and Biophysics, vol. 301, No. 1, dated Feb. 15, 1993, pp. 41-52.

Miners et al., "Decreased Expression and Activity of Neprilysin in Alzheimer Disease Are Associated With Cerebral Amyloid Angiopathy", J Neuropathol Exp Neutrol, vol. 65, No. 10, dated Oct. 2006, pp. 1012-1021.

Moffat et al., "Free testosterone and risk for Alzheimer disease in older men", Neurology, vol. 62, dated Jan. 2004, pp. 188-193.

Moffat et al., "Long-term measures of free testosterone predict regional cerebral blood flow patterns in elderly men", Neurobiology of Aging, vol. 28, dated 2007, pp. 914-920.

Morgentaler et al., "Testosterone Therapy and Cardiovascular Risk: Advances and Controversies", Mayo Clin Proc., vol. 90, No. 2, dated 2015, pp. 224-251.

Morinaga et al., "Estrogen has anti-amyloidogenic effects on Alzheimer's β-amyloid fibrils in vitro", Biochemical and Biophysical Research Communications, vol. 359, dated 2007, pp. 697-702.

Morsink et al., "Associations between sex steroid hormone levels and depressive symptoms in elderly men and women: Results from the Health ABC study", Psychoneuroendocrinology, vol. 32, dated 2007, pp. 874-883.

Papasozomenos et al., "Testosterone prevents the heat shock-induced overactivation of glycogen synthase kinase-3β but not of cyclin-dependent kinase 5 and c-Jun NH-2-terminal kinase and concomitantly abolishes hyperphosphorylation of τ: Implications for Alzheimer's disease", PNAS, vol. 99, No. 3, dated Feb. 5, 2002, pp. 1140-1145.

Pedram et al., "Estrogen Inhibits Cardiac Hypertrophy: Role of Estrogen Receptor-β to Inhibit Calcineurin", Endocrinology, vol. 149, No. 7, dated Jul. 2008, pp. 3361-3369.

Pedram et al., "Estrogen Receptor-β Prevents Cardiac Fibrosi" Mol Endocrinol, vol. 24, No. 11, dated 2010, pp. 2152-2165.

Phillips et al., "Association of Hyperestrogenemia and Coronary Heart Disease in Men in the Framingham Cohort", The American Journal of Medicine, vol. 74, dated May 1983, pp. 863-869.

Pirskanen et al., "Estrogen receptor beta gene variants are associated with increased risk of Alzheimer's disease in women", European Journal of Human Genetics, vol. 13, dated 2005, pp. 1000-1006.

Ready et al., "Testosterone deficiency and apathy in Parkinson's disease: a pilot study", J Neural Neurosurg Psychiatry, vol. 75, dated 2004, pp. 1323-1326.

Resnick et al., "Testosterone Treatment and Cognitive Function in Older Men With Low Testosterone and Age-Associated Memory Impairment", JAMA, vol. 317, No. 7, dated Feb. 21, 2017, pp. 717-727.

Rhoden et al., "Treatment of testosterone-induced gynecomastia with the aromatase inhibitor, anastrozole", International Journal of Impotence Research, vol. 16, dated 2004, pp. 95-97.

Ricke et al., "Prostatic hormonal carcinogenesis is mediated by in situ estrogen production and estrogen receptor alpha signaling", The FASEB Journal, vol. 22, dated May 2008, pp. 1512-1520.

Risbridger et al., "Estrogen action on the prostate gland: a critical mix of endocrine and paracrine signaling", Journal of Molecular Endocrinology, vol. 39, dated 2007, pp. 183-188.

Rizza et al., "Estrogen receptor beta as a novel target of androgen receptor action in breast cancer cell lines", Breast Cancer Research, vol. 16, dated 2014 in 13 pages.

Salom et al., "Relaxant Effects of 17-β-Estradiol in Cerebral Arteries Through $Ca^{2+}$ Entry Inhibition", Journal of Cerebral Blood Flow and Metabolism, vol. 21, No. 4, dated 2001, pp. 422-429.

Schutter et al., "Administration of Testosterone Increases Functional Connectivity in a Cortico-Cortical Depression Circuit", J Neuropsychiatry Clin Neurosci, vol. 17, No. 3, dated 2005, pp. 372-377.

Shumaker et al., "Conjugated Equine Estrogens and Incidence of Probable Dementia and Mild Cognitive Impairment in Postmenopausal Women", JAMA, vol. 291, No. 24, dated Jun. 2004, pp. 2947-2958.

Shumaker et al., "Estrogen Plus Progestin and the Incidence of Dementia and Mild Cognitive Impairment in Postmenopausal Women", JAMA, vol. 289, No. 20, dated May 28, 2003, oo. 2651-2662.

Smith, "The aging process: where are the drug opportunities?", Current Opinion in Chemical Biology, vol. 4, dated 2000, pp. 371-376.

Syed et al., "Patterns of regional cerebral blood flow in Alzheimer's disease", Nuclear Medicine Communications, vol. 13, dated 1992, pp. 656-663.

Tan et al., "Myocardial Infarction and Stroke Risk in Young Healthy Men Treated with Injectable Testosterone", International Journal of Endocrinology, dated 2015 in 8 pages.

"The Impact of Testosterone Therapy in Men on Cardiovascular Risk: Don't Be Too Quick to Condemn", Mayo Clinic Proceedings, vol. 90, No. 2, dated Feb. 2015, pp. 163-165.

Tolba et al., "Caffeic Acid Phenethyl Ester Synergistically Enhances Docetaxel and Paclitaxel Cytotoxicity in Prostate Cancer Cells", International Union of Biochemistry and Molecular Biology, vol. 65, No. 8, dated Aug. 2018, pp. 716-729.

Traish et al., "Long-Term Testosterone Therapy Improves Cardiometabolic Function and Reduces Risk of Cardiovascular Disease in Men with Hypogonadism: A Real-Life Observational Registry Study Setting Comparing Treated and Untreated (Control) Groups", Journal of Cardiovascular Pharmacology and Therapeutics, vol. 22, No. 5, dated 2017, pp. 414-433.

Tyler et al., "α- and β-secretase: profound changes in Alzheimer's disease", Biochemical and Biophysical Research Communications, vol. 299, dated 2002, pp. 373-376.

Vigen et al., "Association of Testosterone Therapy With Mortality, Myocardial Infarction, and Stroke in Men With Low Testosterone Levels", JAMA, vol. 310, No. 17, dated 2013, pp. 1829-1836.

Vincent et al., "Activation of the ∝-Secretase Processing of AβPP as a Therapeutic Approach in Alzheimer's Disease", Journal of Alzheimer's Disease, vol. 24, dated 2011, pp. 75-94.

Wittert, "The relationship between sleep disorders and testosterone in men", Asian Journal of Andrology, dated 2014, pp. 262-265.

Xu et al., "Estrogen reduces neuronal generation of Alzheimer β-amyloid peptides", Nature Medicine, vol. 4, No. 4, dated Apr. 1998, pp. 447-451.

Yao et al., "Androgens regulate neprilysin expression: role in reducing β-amyloid levels", Journal of Neurochemistry, vol. 105, dated 2008, pp. 2477-2488.

Younkin, "The role a Aβ42 in Alzheimer's disease", J Physiology (Paris), vol. 92, dated 1998, pp. 289-292.

Ysrraelit et al., "Impact of Andropause on Multiple Sclerosis", Frontiers in Neurology, vol. 12, dated Nov. 2021, in 6 pages.

Zhao et al., "Early Intervention with an Estrogen Receptor β-Selective Phytoestrogenic Formulation Prolongs Survival, Improves Spatial Recognition Memor, and Slows Progression of Amyloid Pathology in a Female Mouse Model of Alzheimer's Disease", J Alzheimers Dis., vol. 37, No. 2, dated 2013, pp. 403-419.

Zhu et al., "Quantitative Structure-Activity Relationship of Various Endogenous Estrogen Metabolites for Human Estrogen Receptor ∝ and β Subtypes: Insights into the Structural Determinants Favoring a Differential Subtype Binding", Endocrinology, vol. 147, No. 9, dated Sep. 2006, pp. 4132-4150.

Zitzmann et al., "Changes in cerebral glucose metabolism and visuospatial capability in hypogonadal males under testosterone

(56) References Cited

OTHER PUBLICATIONS substitution therapy", Experimental and Clinical Endocrinology & Diabetes, vol. 109, dated 2007, pp. 302-304.
Davis et al., "Global Consensus Position Statement on the Use of Testosterone Therapy for Women", The Journal of Clinical Endocrinology & Metabolism, 2019, 10 pages.
Center for Drug Evaluation and Research, Testosterone information. Food and Drug Administration, https://www.fda.gov/drugs/postmarket-drug-safety-information-patients-and-providers/testosterone-information#:~:text=Testosterone%20products%20are%20FDA%2Dapproved.as%20genetic%20problems%20or%20chamotherapy, dated Mar. 3, 2015, in 1 page.
Henderson, Victor W., "Alzheimer's disease: Review of hormone therapy trials and implications for treatment and prevention after menopause", Journal of Steroid Biochemistry & Molecular Biology, 142, 2014, 99-106.
Jenkins et al., "How Dangerous is Testosterone Supplementation?", Editor's Comment, vol. 41, 2015, pp. 195-198.
Pardridge et al., "Effects of human serum on transport of testosterone and estradiol into rat brain. Am J Physiol", Feb. 26, 1980, in 6 pages.

\* cited by examiner

COMBINATION HORMONE FORMULATIONS AND THERAPIES

CROSS REFERENCE TO RELATED APPLICATIONS

This patent application claims the benefit of priority to U.S. Provisional Application No. 62/910,227, filed Oct. 3, 2019, and U.S. Provisional Application No. 62/910,225, filed Oct. 3, 2019. All of the foregoing applications are fully incorporated herein by reference in their entireties for all purposes.

FIELD

The disclosure relates to combination therapies and methods of making and using thereof.

BACKGROUND

Alzheimer's disease (AD) is a neurodegenerative disorder that leads to progressive memory loss, impairments in behavior, language, visuospatial skills, and ultimately death. The disease is associated with and defined by neuronal and synaptic loss, the presence of extracellular deposits of β-amyloid protein, and intracellular formation of neurofibrillary tangles in the brain. AD patients have alterations in their brain chemistry that favor the formation of these plaques and tangles. In the study of cancer, bacteria, or viruses, it is a matter of course that natural selection will result in mutations advantageous to the invading organism. However, cell divisional is not applicable in the case of AD, therefore natural selection is not a factor.

Currently, an estimated 5.7 million Americans have AD and by 2050 it is projected that 13.8 million Americans will have it. AD is the sixth leading cause of death in the United States. It is estimated that the total cost for everyone alive today in the United States who will eventually develop AD is $47.1 trillion. The six drugs currently approved by the FDA for the treatment of AD temporarily improve symptoms for some people, but do nothing to slow or stop the progression of the disease. Approximately 491,000 new cases of AD and dementia are expected in 2020 for people aged 65 or older.

SUMMARY

Disclosed herein are compositions and methods useful for the treatment or amelioration of various diseases, disorders, or conditions.

Some embodiments pertain to a composition comprising a testosterone source (e.g., testosterone, a testosterone precursor, etc.). In some embodiments, the composition comprises an aromatase inhibitor. In some embodiments, the composition comprises an estriol source (e.g., estriol, an estriol precursor, etc.). In some embodiments, the composition comprises a progesterone source (e.g., progesterone, a progesterone precursor, etc.). In some embodiments, the composition comprises a glucocorticoid. Some embodiments pertain to a composition comprising or consisting essentially of a testosterone source, an aromatase inhibitor, and an estriol source. In some embodiments, the composition comprises a progesterone source. Some embodiments pertain to a composition comprising or consisting essentially of a testosterone source, an aromatase inhibitor, an estriol source, and a progesterone source. In some embodiments, the composition comprises a glucocorticoid (and/or a glucocorticoid source) or one or more glucocorticoids. Some embodiments pertain to a composition comprising or consisting essentially of a testosterone source, an aromatase inhibitor, an estriol source, and a glucocorticoid. Some embodiments pertain to a composition comprising or consisting essentially of a testosterone source, an aromatase inhibitor, an estriol source, a progesterone source, and a glucocorticoid. In some embodiments, the testosterone source is testosterone. In some embodiments, the estriol source is estriol. In some embodiments, the progesterone source is progesterone. In some embodiments, the aromatase inhibitor is selected from anastrozole, letrozole, exemestane, or combinations thereof. In some embodiments, the composition lacks one or more of a testosterone source, an aromatase inhibitor, an estriol source, a progesterone source, and/or a glucocorticoid.

In some embodiments, the composition comprises a carrier.

In some embodiments, testosterone (and/or the testosterone source) comprises from 1.0-99.5% of a total mass of the composition. In some embodiments, the estriol source comprises from 10-60% of the total mass of the composition. In some embodiments, the aromatase inhibitor comprises from 0.5-50% of the total mass of the composition. In some embodiments, the one or more glucocorticoids comprises from 0-50% of the total mass of the composition. In some embodiments, the carrier comprises from 0-80% of the total mass of the composition.

In some embodiments, the composition further comprises phytoestrogen. In some embodiments, the composition further comprises vitamin D3. In some embodiments, the composition further comprises one or more androgens. In some embodiments, the androgens comprise dehydroepiandrosterone sulfate. In some embodiments, the androgens comprise androstenedione. In some embodiments, the composition lacks one or more of these agents.

In some embodiments, the composition is provided as a unit dose. In some embodiments, the composition is provided as a pellet. In some embodiments, the pellet has a mass from 100-600 milligrams (mg), or from 290-310 mg, or from 145-155 mg or from 75-85 mg. In some embodiments, the composition comprises a pharmaceutically acceptable excipient. In some embodiments, the composition comprises an excipient that is capable of releasing testosterone and the aromatase inhibitor in the blood at a controlled rate for a period of at least 30 days.

Some embodiments pertain to a method of producing super-physiologically high levels of testosterone in a subject by administering an effective amount of a composition described herein. In some embodiments, the method comprises administering a composition as disclosed herein to a subject every 10 weeks to 14 weeks. In some embodiments, the composition is administered in a cyclic administration of progesterone in which high levels of progesterone are achieved 10 days in a row. In some embodiments, the subject is a male. In some embodiments, the composition is configured to raise the male's free testosterone level by (or to) equal to or greater than about 24 ng/dL. In some embodiments, the composition is configured to raise the male's free testosterone level from about 24 ng/dL to about 45 ng/dL. In some embodiments, the subject is a female. In some embodiments, the composition is configured to raise the subject's free testosterone level by (or to) equal to or greater than about 2 ng/dL. In some embodiments, the composition is configured to raise the female subject's free testosterone level from about 10 ng/dL to about 25 ng/dL. In some embodiments, the composition is configured to raise the free testosterone level from about 240 ng/dL to about 450 ng/dL. In some embodiments, the composition is configured to raise the subject's free testosterone level from about 100 ng/dL to about 250 ng/dL.

In some embodiments, the composition is configured to inhibit the conversion of testosterone to estradiol. In some embodiments, the composition is configured to reduce β-amyloids in a subject.

Some embodiments pertain to treating a subject. In some embodiments, an effective amount of the composition is administered subcutaneously. In some embodiments, an effective amount of the composition is administered orally. Some embodiments pertain to a method of downregulating β-secretase activity in a subject by administering an effective amount of a composition as described herein to a subject.

Some embodiments pertain to a method of upregulating α-secretase activity in a subject by administering an effective amount of a composition as described herein to a subject.

Some embodiments pertain to a method of upregulating neprilysin activity in a subject by administering an effective amount of a composition as described herein to a subject.

There exists a continuing need for an effective approach for treating, mitigating, slowing the progression of, and preventing Alzheimer's disease. Some embodiments disclosed herein pertain to a method of treating or preventing Alzheimer's disease. In some embodiments, the method comprises administering to a subject in need of treatment a composition as disclosed elsewhere herein. In some embodiments, as disclosed elsewhere herein, the composition comprises a combination of a testosterone source, an aromatase inhibitor, and an estriol source. In some embodiments, the testosterone source is testosterone. In some embodiments, the estriol source is estriol. In some embodiments, the combination further comprises progesterone. In some embodiments, the combination further comprises a glucocorticoid. In some embodiments, each active agent in the combination is administered sequentially. In some embodiments, each active agent is administered in substantially simultaneously.

Some embodiments pertain to a method of treating and/or preventing Alzheimer's disease. In some embodiments, the method comprises administering to a subject in need of treatment the composition as described elsewhere herein. In some embodiments, the subject's β-amyloid 42/β-amyloid 40 ratio is lowered. In some embodiments, the composition improves the subject's brain glucose metabolism. In some embodiments, the composition improves the subject's cerebral blood flow. In some embodiments, the composition prevents or substantially prevents the hyperphosphorylation of the tau protein. In some embodiments, the composition reduces β-amyloids in the subject's brain. In some embodiments, the testosterone levels of a subject are raised to about 1000 ng/dL to 10,000 ng/dL. In some embodiments, the testosterone levels of a subject are raised by at least 200%. In some embodiments, the composition is taken while the subject is on a MIND diet. In some embodiments, the composition reduces cardiac arrest and stroke in a subject. In some embodiments, the subject has a testosterone level of 350 ng/dL or less before treatment. In some embodiments, the subject is male. In some embodiments, the subject is female. In some embodiments, the female subject's testosterone level is increased to 300 ng/dL or higher. In some embodiments, the activity of estrogen receptor-β is increased.

Some embodiments pertain to a method of treating or ameliorating a disease in a subject, the method comprising: administering an effective amount of the composition as described elsewhere herein. In some embodiments, the disease is a cancer. In some embodiments, the cancer is breast cancer, ovarian cancer, or prostate cancer. In some embodiments, the disease is Parkinson's disease, type II diabetes, or metabolic syndrome. In some embodiments, the composition comprises an aromatase inhibitor. In some embodiments, the composition comprises an estriol source. In some embodiments, the composition comprises a testosterone source, an aromatase inhibitor, and an estriol source. In some embodiments, the composition comprises a progesterone source. In some embodiments, the composition comprises a glucocorticoid. In some embodiments, the testosterone source is testosterone. In some embodiments, the estriol source is estriol. In some embodiments, the progesterone source is progesterone. In some embodiments, the aromatase inhibitor is selected from anatrozole, letrozole, exemestane, or combinations thereof. In some embodiments, the composition lacks one or more of a testosterone source, an aromatase inhibitor, an estriol source, a progesterone source, and/or a glucocorticoid. In some embodiments, the composition further comprises, at least one of, phytoestrogen, vitamin D3, progesterone, androgen, dehydroepiandrosterone sulfate, androstenedione, and a glucocorticoid. In some embodiments, treating or ameliorating a disease is treating symptoms of the disease.

Some embodiments pertain to a method increasing longevity in a subject by administering to a subject in need of treatment an effective amount of the composition described herein.

Some embodiments pertain to a method of increasing survival time in a subject by administering to a subject in need of treatment an effective amount of the composition as described herein.

Some embodiments pertain to a method of increasing life span in a subject by administering to a subject in need of treatment an effective amount of the composition as described herein.

Some embodiments pertain to a method of increasing health span in a subject by administering to a subject in need of treatment an effective amount of the composition as described herein.

Some embodiments pertain to a composition comprising or consisting essentially of a testosterone source, an aromatase inhibitor, and an estriol source. Some embodiments pertain to a composition comprising or consisting essentially of a testosterone source, an aromatase inhibitor, an estriol source, and a progesterone source. Some embodiments pertain to a composition comprising or consisting essentially of a testosterone source, an aromatase inhibitor, an estriol source, and a glucocorticoid. Some embodiments pertain to a composition comprising or consisting essentially of a testosterone source, an aromatase inhibitor, an estriol source, a progesterone source, and a glucocorticoid. Some embodiments pertain to a composition comprising or consisting essentially of testosterone, an aromatase inhibitor, and estriol. Some embodiments pertain to a composition comprising or consisting essentially of testosterone, an aromatase inhibitor, estriol, and progesterone. Some embodiments pertain to a composition comprising or consisting essentially of testosterone, an aromatase inhibitor, estriol, and a glucocorticoid. Some embodiments pertain to a composition comprising or consisting essentially of testosterone, an aromatase inhibitor, estriol, progesterone, and a glucocorticoid. Some embodiments pertain to a composition comprising or consisting essentially of testosterone, an aromatase inhibitor, estriol, progesterone, and dexamethasone. Some embodiments pertain to a composition comprising or consisting essentially of testosterone, an aromatase inhibitor, estriol, progesterone, and hydrocortisone. Some embodiments pertain to a composition comprising or consisting essentially of testosterone, an aromatase inhibitor, estriol, and dexamethasone. Some embodiments pertain to a composition comprising or consisting essentially of testosterone, an aromatase inhibitor, estriol, and hydrocortisone.

Not all objectives mentioned in this specification are achieved in all embodiments disclosed and/or claimed herein.

DETAILED DESCRIPTION

Figure 1:
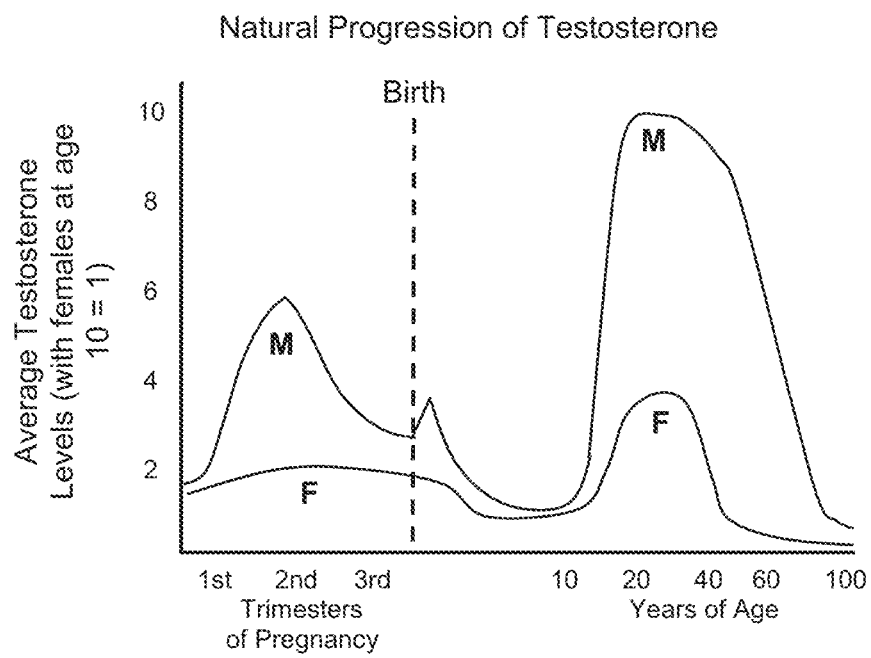
FIG. 1 is a graph showing the natural progression of testosterone levels in humans throughout life.

Disclosed herein are compositions and methods useful for the prevention, treatment, and/or amelioration of various diseases, disorders, or conditions. Some embodiments pertain to a composition comprising a testosterone source (e.g., testosterone). In some embodiments, the composition further comprises an aromatase inhibitor. In some embodiments, the composition further comprises an estriol source (e.g., estriol). In some embodiments, the composition further comprises a progesterone source (e.g., progesterone). In some embodiments, the composition further comprises a glucocorticoid (e.g., hydrocortisone). In some embodiments, the composition comprises dexamethasone (or further comprises). In some embodiments, the composition lacks one or more of a testosterone source, an aromatase inhibitor, an estriol source, a progesterone, and/or a glucocorticoid. Also presented herein is the surprising discovery that exposing a subject to compositions as disclosed herein can increase one or more of a subject's longevity, survival time, life span, and health span, and/or can treat Alzheimer's disease.

The section headings used herein are for organizational purposes only and are not to be construed as limiting the subject matter described. Features disclosed under one heading (such as a composition) can be used in combination with features disclosed under a different heading (a method of treating). Unless defined otherwise, all technical and scientific terms used herein have the same meaning as is commonly understood by one of ordinary skill in the art. It should be noted that the use of particular terminology when describing certain features or aspects of the disclosure should not be taken to imply that the terminology is being re-defined herein to be restricted to include any specific characteristics of the features or aspects of the disclosure with which that terminology is associated.

While the disclosure has been illustrated and described in detail in the foregoing description, such description is to be considered illustrative or exemplary and not restrictive. The disclosure is not limited to the disclosed embodiments. Variations to the disclosed embodiments can be understood and effected by those skilled in the art in practicing the claimed disclosure, from a study of the disclosure and the appended claims.

As used in the specification and the appended claims, the singular forms "a," "an" and "the" include plural referents unless the context clearly dictates otherwise. The use of "or" or "and" means "and/or" unless stated otherwise. Furthermore, use of the term "including" as well as other forms, such as "include", "includes," and "included," is not limiting. The mere fact that certain measures are recited in mutually different dependent claims does not indicate that a combination of these measures cannot be used to advantage.

Where a range of values is provided, it is understood that the upper and lower limit, and each intervening value between the upper and lower limit of the range is encompassed within the embodiments.

The term "subject" includes animals (for example, mammals, for example, cats, dogs, horses, pigs, cows, sheep, rodents, rabbits, squirrels, camels, bears, primates (for example, chimpanzees, gorillas, and/or humans)). It also includes transgenic animal models.

It is understood that the methods and formulations described herein include the use of pharmaceutically acceptable salts and/or conformers of compounds of disclosed embodiments, as well as metabolites and active metabolites of these compounds having the same type of activity. A conformer is a structure that is a conformational isomer. Conformational isomerism is the phenomenon of molecules with the same structural formula but different conformations (conformers) of atoms about a rotating bond. Likewise, it is understood that the compounds described herein, include the compound in any of the forms described herein (e.g., pharmaceutically acceptable salts, enantiomeric forms, tautomeric forms, and the like).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, C1-C7 alkylamine, cyclohexylamine, triethanolamine, ethylenediamine, and salts with amino acids such as arginine and lysine.

The terms "effective amount" and "therapeutically effective amount" are broad terms, and are to be given their ordinary and customary meaning to a person of ordinary skill in the art (and are not to be limited to a special or customized meaning), and refer without limitation to a sufficient amount of an agent or a compound being administered which will relieve to some extent one or more of the symptoms of the disease and/or condition being treated. In some embodiments, the result can be reduction and/or alleviation of the signs, symptoms, or causes of a disease, or any other desired alteration of a biological system. For example, an "effective amount" for therapeutic uses is an amount of the composition comprising a compound as disclosed herein required to provide a clinically significant decrease in disease symptoms. An appropriate "effective" amount in any individual case may be determined using techniques, such as a dose escalation study. Where a drug has been approved by the U.S. Food and Drug Administration (FDA) or a counterpart foreign medicines agency, a "therapeutically effective amount" optionally refers to the dosage approved by the FDA or its counterpart foreign agency for treatment of the identified disease or condition.

The term "bioavailability" includes, generally, the degree to which a drug or other substance (e.g., testosterone) becomes available to a subject following ingestion, administration, or exposure. In one embodiment, for example, the bioavailability of one or more of the compounds disclosed herein may be the bioavailability to a particular target tissue (e.g., the brain). For example, in an embodiment, the particular target tissue may require traversal of the stomach, the small intestines, and/or the blood brain barrier, therefore the bioavailability data may be obtained from this particular target tissue.

The terms "treat," "treatment," or "treating," as used herein refers to administering a compound or pharmaceutical composition to a subject for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition.

The term "co-administration" and similar terms as used herein are broad terms, and are to be given their ordinary and customary meaning to a person of ordinary skill in the art (and are not to be limited to a special or customized meaning), and refer without limitation to administration of the selected therapeutic agents to a single patient, and are intended to include treatment regimens in which the agents are administered by the same or different route of administration or at the same or different time. In some embodiments, the compounds disclosed herein are co-administered.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' preferred, 'desired,' or 'desirable,' and words of similar meaning should not be understood as implying that certain features are critical, essential, or even important to the structure or function of the disclosure, but instead as merely intended to highlight alternative or additional features that may or may not be utilized in a particular embodiment of the disclosure. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Additionally, the phrase "consisting essentially of" will be understood to include those elements specifically recited and those additional elements that do not materially affect the basic and novel characteristics of the claimed technology. The phrase "consisting of" excludes any element not specified. The transitional phrase "consisting of" excludes any element, step, or ingredient not specified in the claim.

"Longevity" refers to the time for which a subject is expected to live, based on the year of the subject's birth, the subject's current age, and the progression of a disease state of the subject. It may further include subject-specific demographics or determinants such as gender, genetics, lifestyle (such as smoking, physical exercise, activity in everyday life, alcohol consumption, diet, self-care practices, social contacts and work-style), culture, politics, religion, and socioeconomics. See, e.g., "Men, Ageing and Health," (2001), 01/WHO/NMH/NPH 01.2

"Survival time" refers to the expected duration of time until death of a subject. It may further include subject-specific demographics or determinants such as gender, genetics, lifestyle, culture, politics, religion, and socioeconomics.

"Lifespan" refers to the expected duration of life that a subject has remaining at a given age with consideration of the subject's state of health (e.g., the progress of a disease state of the subject). It may further include subject-specific demographics or determinants such as gender, genetics, lifestyle, culture, politics, religion, and socioeconomics.

"Health span" refers to the expected length of time in a subject's life during which a subject is in reasonably good health. In some embodiments, a subject's health considers one or more of physical, mental (e.g., lucidity), social-well-being, absence of disease, and absence of infirmity.

The term "increase" referred to in the disclosed embodiments refers to an "expected increase" for the subject as opposed to the actual increase any particular subject experiences. Thus, one does not need to wait for a subject's longevity, survival time, life span, or health span to expire in order to practice the disclosed embodiments. Expected increases may be statistically significant or insignificant, though in some embodiments any expected increase is statistically significant. There are many methods known for calculating statistical significance, e.g., calculating a "p-value." In some embodiments, the threshold for statistical significance is a p-value $\leq 0.2, \leq 0.15$, $\leq 0.1$, $\leq 0.05$, $\leq 0.01$, $\leq 0.005$, about $\leq 0.2$, about $\leq 0.15$, about $\leq 0.1$, about $\leq 0.05$, about $\leq 0.01$, or about $\leq 0.005$. Sometimes, a result may not be statistically significant but yet the result is still informative or suggestive of some conferred benefit. It is understood that the degree of significance one would ascribe to a particular result is within the ken of the ordinarily skilled physician.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviations, per the practice in the art. Alternatively, "about" can mean a range of up to 20%, up to 10%, up to 5%, and up to 1% of a given value. Alternatively, particularly with respect to biological systems or processes, the term can mean within an order of magnitude, within 5-fold, and within 2-fold, of a value. Where particular values are described in the application and claims, unless otherwise stated the term "about" meaning within an acceptable error range for the particular value should be assumed.

The term "pharmaceutical composition" refers to a mixture of one or more compounds disclosed herein with other chemical components, such as diluents or carriers. The pharmaceutical composition facilitates administration of the compound to an organism. Pharmaceutical compositions will generally be tailored to the specific intended route of administration.

As used herein, a "carrier" refers to a compound that facilitates the delivery of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

As used herein, the term "weight percent," when referring to a component, is the weight of the component divided by the weight of the composition that includes the component, multiplied by 100%. For example the weight percent of component A when 5 grams of component A is added to 95 grams of component B is 5% (e.g., 5 g A/(5 g A+95 g B)×100%).

Introduction

Several embodiments pertain to therapy (e.g., hormone therapy) to ameliorate conditions associated with Alzheimer's disease (AD). A first concept of the hormone therapy disclosed herein is to reduce the extracellular plaque deposits associated with AD which are composed primarily of β-amyloid proteins (sometimes referred to as Aβ herein or as β-amyloids). β-amyloid proteins are created by the cleavage of the amyloid precursor protein (APP) first by β-secretase and then by γ-secretase. Another enzyme, α-secretase, cleaves APP at a spot within the β-amyloids sequence and thus prevents the formation of β-amyloids. Although excess levels of β-amyloids are involved in the development of AD, there is a range of β-amyloids which is necessary to maintain the proper functioning of the synapses within the brain. In patients with AD, there is a large decrease in α-secretase activity and a large increase in β-secretase activity. It is believed that both testosterone (T) and estradiol (sometimes referred to as E2 herein) reduce the neuronal generation of Aβ. A study on mice showed that a cyclic administration of progesterone (sometimes referred to as P4 herein) in which high levels of progesterone were achieved 10 days in a row every 30 days decreased Aβ levels and enhanced the decrease that estradiol alone produced. Without being bound to a particular theory, it is believed that T reduces total β-amyloids because T may downregulate β-secretase activity, upregulate α-secretase activity, and upregulate neprilysin activity. As shown in FIG. 1, testosterone levels fluctuate during a subject's life and tend to start decreasing dramatically around 40 years old. In some embodiments, the compositions disclosed herein can be used to raise testosterone (e.g., free testosterone) to physiological or supraphysiological levels. Neprilysin is an enzyme which may break down both β-amyloid monomers and β-amyloid oligomers. Estradiol also may downregulate β-secretase activity, upregulate neprilysin activity, and upregulate α-secretase activity. Without being bound, this may explain how estradiol may act to reduce total β-amyloids. To add to the complexity regarding progesterone, continual high levels of progesterone actually negates the downregulation of β-amyloid production caused by estradiol. Among all kinds of Aβ isoforms, Aβ40 and Aβ42 are believed to be the most important ones. Although these two kinds of Aβ differ only in two amino acid residues, recent studies show that they differ significantly in their metabolism, physiological functions, toxicities, and aggregation mechanism. In preventing Alzheimer's, it may be important to reduce the Aβ42/Aβ40 ratio. T reduces the Aβ42/Aβ40 ratio as does estradiol.

In several embodiments, the hormone therapy disclosed herein is used to prevent the hyperphosphorylation of the tau protein. It is believed that estradiol has no effect on this hyperphosphorylation, but progesterone downregulates tau hyperphosphorylation, whether given continually or for 10 days in a row to every 30 days.

In several embodiments, the hormone therapy disclosed herein is used to enhance brain glucose metabolism. Estradiol may be used to enhance metabolism though the role of progesterone on brain glucose metabolism proven. Cerebral blood flow is impaired in those with AD. T improves cerebral blood flow as does estradiol. Progesterone does not have any effect on cerebral blood flow.

In some embodiments, the hormone therapy may be used in combination with a Mediterranean-DASH Intervention for Neurogenerative Delay (MIND) diet to reduce risk of developing AD. In a study, the subjects on a MIND diet were divided into tertiles depending on how closely they followed the diet. The tertile that was most compliant had 47% of the risk of developing AD as compared to those in the most non-compliant tertile. Even the middle tertile had 65% of the risk. People who smoked more than two packs of cigarettes per day more than doubled their risk of developing AD. AD is correlated with air pollution. People living in cities with the highest tertile of air pollution increase their risk of developing AD more than 4-fold as compared to those living in cities with the lowest tertile. Autopsy studies showed that people living in heavily polluted cities accumulated over 4 times as much Aβ42 in their brains as people living in cities with low levels of air pollution. Long term exposure to both coarse and fine particulate matter air pollution leads to significantly faster cognitive decline in older women. Mice that were exposed to a nickel nanoparticle-enhanced atmosphere for 3 hours more than doubled the Aβ42 levels in their brains 24 hours later. However, just a MIND diet alone does not completely ameliorate Alzheimer's. Other dietary factors and nutritional supplements should be tested with regards to Alzheimer's in order to see what else should be added to, or eliminated from, one's diet in order to minimize the risk of developing Alzheimer's.

In several embodiments, the disclosed hormone therapy is used to produce a sufficiently high level of T that will prevent AD in men. The risks of administering T to men are potentially causing too much estradiol and too many red blood cells. Both of these conditions can be monitored and treated. There has been a claim that T increases the risks of heart attacks and strokes in men. However, it is believed that T may be extremely effective in preventing heart attacks and strokes in men whose starting T is 350 ng/dL or less. T may also be very useful in treating men after they have suffered a heart attack.

While some doctors may have some concern that T may cause prostate cancer (sometimes referred to as PCa herein) in men, T may only be a secondary cause of prostate cancer. The primary cause may be high local levels of estradiol within the epithelial cells of the prostate. In some embodiments, T seems to be beneficial against early stage prostate cancer. A 12-year study of hypogonadal men showed that those men who received T had a 2.7% rate of prostate cancer vs. 8.9% for those men who did not receive T, with none of the treated men being diagnosed with prostate cancer after the first 18 months. The percentage of men with occult prostate cancer tumors should have been roughly the same in both groups. This means that for the men treated with T who did not develop prostate cancer, at best, T killed all of the prostate cancer present and at worst, T slowed down the growth rate of the occult prostate cancer tumors to such an extent that they never grew large enough to be detected. This finding in no way disputes the fact that the absence of T is capable of killing most prostate cancer. The absence of T and the presence of high T kill prostate cancer using different mechanisms. Because it is known that too high a level of estradiol or too high a hematocrit level is dangerous, experiments may be done with increasing levels of T while monitoring and controlling estradiol and hematocrit levels in order to determine whether T is dangerous. For example, T may worsens sleep apnea in some men, but it is not known whether this is due to the increased level of T or the increased level of estradiol. In this study both the T and estradiol levels increased 2 to 3-fold. The authors assumed that T was the sole cause for the results they observed, but they did nothing to rule out estradiol in spite of the fact that for severely obese men, the severity of obstructive sleep apnea is inversely proportional to their free T level.

It is believed that high enough levels of T should prevent and possibly halt the progression of AD in men. However, using such high levels long term in women may not be feasible due to the masculinizing effects of T. However, it is possible AD may be prevented in women by using a combination of T, estrogen, and progesterone. High enough levels may even stop the progression of early stage AD.

It is believed that T serum levels as high as 299 ng/dL can be safely used in women. This level even significantly reduced the risk of breast cancer. A study involving lean elderly women showed that the free androgenization index (FAI) was 0.377 for those women with AD as opposed to 1.163 for those women without AD. Low free T levels may increase women's risk of developing AD. The more than 3-fold difference in the FAI is especially striking.

Figure 2:
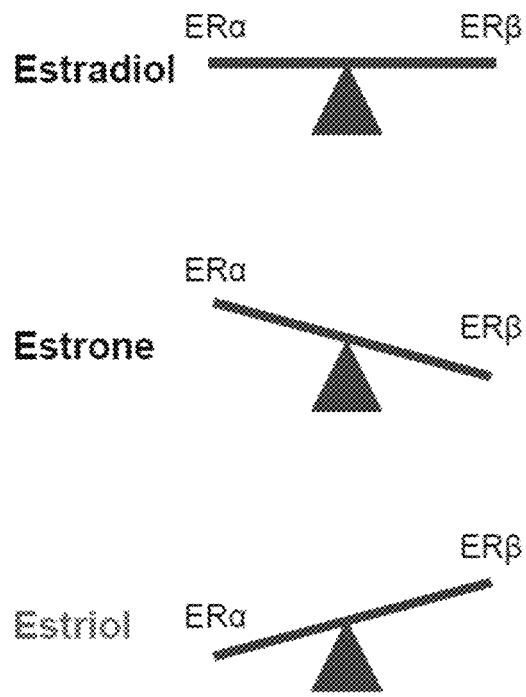
FIG. 2 is a diagram showing the effects of three estrogen hormone compounds on estrogen receptor alpha (ERα) and estrogen receptor beta (ERβ).

It is believed that estrogen receptor beta (ER-β) is protective against AD for females, which raises the question about what effect estrogen receptor alpha (ER-α) has on AD. Since estradiol binds equally well to ER-α and ER-β, experiments involving estradiol can be done with estriol (sometimes referred to as E3 herein) used as well. Estriol binds to ER-α ~9 times more weakly than estradiol does and binds to ER-β ~3 times more weakly than estradiol does. However, in spite of the weaker binding of estriol to both estrogen receptors, estriol may be more effective than estradiol in preventing β-amyloid aggregation, which is an event leading to the formation of AD. Since estriol is more effective than estradiol, it may be because of the ER-β:ER-α binding strength ratio. In the case of estradiol, the ratio is 1:1, whereas in the case of estriol the ratio is 3.2:1. It is believed that ER-β may be effective in combating AD, and that the reason that estriol is more effective than estradiol is likely because ER-α counteracts the beneficial effects of ER-β to some extent. Therefore, if exogenous estrogen is to be used in preventing or treating AD, it makes sense to use estriol instead of estradiol. Estrone binds five times as strongly to ERα as to ERβ. This is shown conceptually in FIG. 2.

The case for using progesterone in a cyclic manner is very compelling. The 10 high days in a row of progesterone every 30 days roughly approximates the behavior of progesterone in women's menstrual cycle. In addition to testosterone, the androgen precursors dehydroepiandrosterone sulfate (DHEAS) and androstenedione, found in much greater concentrations (up to 103-fold) than testosterone, also decline with age. Higher serum levels of testosterone (supplied by the implant) are necessary to provide adequate amounts of testosterone to the AR, replacing not only testosterone but also the significant contributions of DHEAS and androstenedione to bioavailable testosterone.

As disclosed herein, hormones may counteract the biological processes associated with AD. However, researchers are not pursuing this avenue of treatment. In men, this may be due to unwarranted fears that T will increases the risk of prostate cancer, heart attack, and stroke. There are also unwarranted fears that hormones are too dangerous to administer to women. Since T levels in women drop as they age, blocking the intracellular androgen receptor by 80-95% (as medroxyprogesterone acetate has been shown to do) will be more likely to produce an artificial state of T deficiency the older the woman is. It should also be noted that conjugated equine estrogen contains no estriol, which makes it less likely to be helpful in preventing AD.

Hormone Compositions

In some embodiments, one or more compounds (e.g., active agents, active ingredients, etc.) as disclosed herein (e.g., a testosterone source, an aromatase inhibitor, an estriol source, a progesterone source, a glucocorticoid, etc.) are provided as a composition. Some embodiments described herein relates to a pharmaceutical composition, that can include a therapeutically effective amount of one or more compounds described herein and a pharmaceutically acceptable carrier, diluent, excipient or combination thereof. In some embodiments, the pharmaceutical compositions described herein can be administered to a subject per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

In some embodiments, the composition comprises one or more active agents (e.g., a combination of one or more of a testosterone source, an aromatase inhibitor, an estriol source, a progesterone source, a glucocorticoid, etc.) and a pharmaceutically acceptable carrier or diluent. In some embodiments, the composition may comprise a plurality of active agents, (e.g., a combination of one or more of a testosterone source, an aromatase inhibitor, an estriol source, a progesterone source, a glucocorticoid, etc.). In some embodiments, multiple compositions may be provided via the same or different routes, each composition comprising one or more active agents. As disclosed elsewhere herein, some embodiments provide a composition including at least one hormone, or a pharmaceutically acceptable salts of at least one hormone as described herein.

Figure 3:
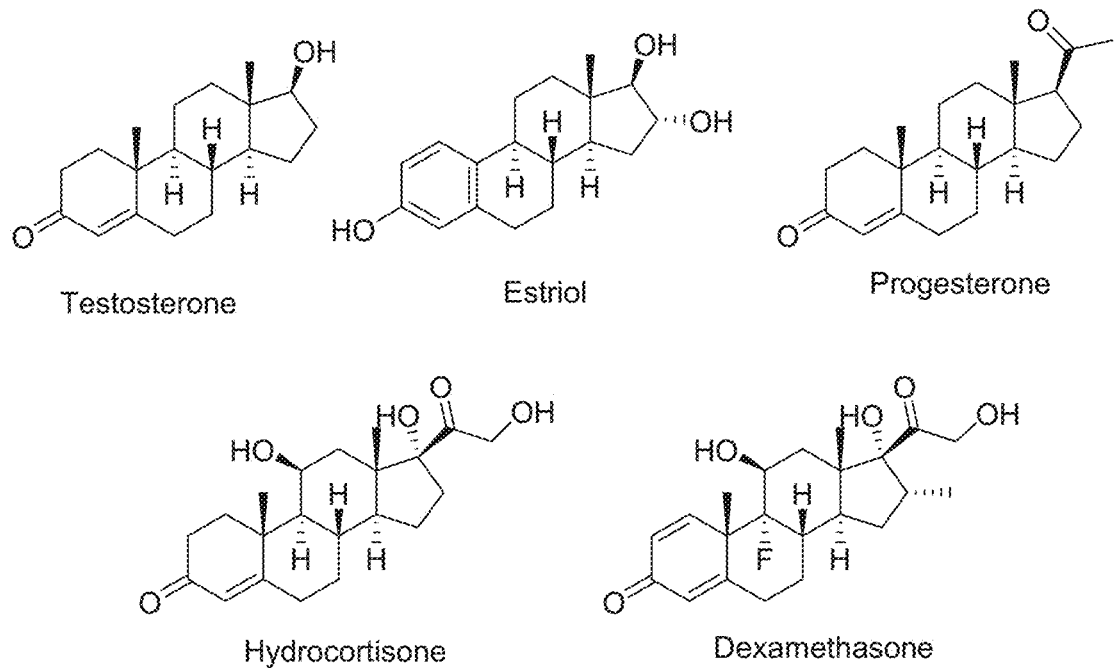
FIG. 3 provides the structure of certain active agents that may be used in one or more embodiments as disclosed herein.

In some embodiments, doses of the one or more active agents are provided to the patient. In some embodiments, the composition includes a dose of a testosterone source. In some embodiments, the testosterone source is testosterone. The structure of testosterone is shown in FIG. 3. In some embodiments, the testosterone source comprises precursors (e.g., prodrugs) of testosterone, testosterone itself, or mixtures of the foregoing. In some embodiments, the testosterone source may include esters of testosterone. In some embodiments, the testosterone esters may include testosterone proprionate, cypionate, enanthate, decanoate, endecanoate, or a combination thereof. In some embodiments, the testosterone source is used in its crystalline form. In some embodiments, the testosterone source is in a noncrystalline or amorphous form. In some embodiments, the testosterone source is provided as a dose. In some embodiments, the amount of testosterone source administered (in mg per day) is equal to or greater than about: 0.1, 1, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 1000, 1500, 1680, 1780, 1980, 2000, 2040, 2180, 2240, 2320, 2560, 2600, 2680, 3000 or ranges including and/or spanning the aforementioned values. In some embodiments, the amount of testosterone source present (in mg) per dose is equal to or greater than about: 0.1, 1, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 1000, 1500, 1680, 1780, 1980, 2000, 2040, 2180, 2240, 2320, 2500, 2560, 2600, 2680, 3000, 3500, 4000, 4500, 5000, 6000, 6760, 7000, 8000, 9000, 10000, or ranges including and/or spanning the aforementioned values. In some embodiments, the testosterone source is in an amount from about 1000 mg to about 3000 mg. In some embodiments, the testosterone source is in an amount from about 1500 mg to about 2500 mg. In some embodiments, the testosterone source is an amount from about 1680 mg to about 2640 mg. In some embodiments, the testosterone source is in an amount from about 30 mg to 200 mg. In some embodiments, the testosterone source is in an amount from about 50 mg to 90 mg.

In some embodiments, the weight percent of testosterone in the composition is equal to or greater than about: 5, 10, 20, 30, 40, 50, 60, 70, 80, 90, 95 or 99, 99.5 or ranges including and/or spanning the aforementioned values.

In some embodiments, as disclosed elsewhere herein, the composition includes an aromatase enzyme inhibitor, also referred to as an aromatase inhibitor. In some embodiments, the composition comprises an aromatase inhibitor source. In some embodiments, the aromatase inhibitor source comprises precursors (e.g., prodrugs) of aromatase inhibitor, an aromatase inhibitor itself, or mixtures of the foregoing. Examples of the aromatase inhibitor may include but are not limited to aminogluthetimide, anastrozole, exemestane, formestane, letrozole, vorozole, 4-androstene-3,6,17-trione, 1,4,6-androstatrien-3,17-dione, or testolactone. In some embodiments, the amount of aromatase inhibitor administered (in mg per day) is equal to or greater than about: 0.1, 1, 5, 10, 12, 16, 20, 24, 30, 32, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 750, 1000, 1250, 1500, 1750, 2000 or ranges including and/or spanning the aforementioned values. In some embodiments, the amount of aromatase inhibitor present (in mg) per dose is equal to or greater than about: 0.1, 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 750, 1000, 1250, 1500, 1750, 2000 or ranges including and/or spanning the aforementioned values. In some embodiments, the aromatase inhibitor is in an amount of about 1 mg to about 90 mg. In some embodiments, the aromatase inhibitor is in an amount from about 2 mg to about 50 mg. In some embodiments, the aromatase inhibitor is in an amount from about 8 mg to about 32 mg. In some embodiments, the aromatase inhibitor is in an amount from about 12 mg to about 32 mg. In some embodiments, the aromatase inhibitor is in an amount from about 12 mg to about 24 mg. In some embodiments, the aromatase inhibitor is in an amount from about 3 to 14 mg.

In some embodiments, the weight percent of aromatase inhibitor in the composition is equal to or greater than about: 0.5, 1, 2, 5, 10, 20, 30, 40, 50, 60, or ranges including and/or spanning the aforementioned values.

In some embodiments, as disclosed elsewhere herein, the composition includes an estriol source. In some embodiments, the estriol source comprises precursors (e.g., prodrugs) of estriol, estriol itself, or mixtures of the foregoing. In some embodiments, the estriol source is estriol. The structure of estriol is shown in FIG. 3. In some embodiments, the amount of estriol administered (in mg per day) is equal to or greater than about: 0.1, 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 600, 700, 800, 900, 1000, or ranges including and/or spanning the aforementioned values. In some embodiments, the amount of estriol source present (in mg) per dose is equal to or greater than about: 0.1, 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 600, 700, 800, 900, 1000, or ranges including and/or spanning the aforementioned values.

In some embodiments, the weight percent of estriol source in the composition is equal to or greater than about: 1, 2, 5, 10, 20, 30, 40, 50, 60, or ranges including and/or spanning the aforementioned values.

In some embodiments, as disclosed elsewhere herein, the composition includes progesterone. In some embodiments, the composition comprises a progesterone source. In some embodiments, the progesterone source comprises precursors (e.g., prodrugs) of progesterone, progesterone itself, or mixtures of the foregoing. The structure of progesterone is shown in FIG. 3. In some embodiments, the amount of progesterone administered (in mg per day) is equal to or greater than about: 0.1, 1, 2, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500, 600, 700, 800, 900, 1000, or ranges including and/or spanning the aforementioned values. In some embodiments, the amount of progesterone present (in mg) per dose is equal to or greater than about: 0.1, 1, 2, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 600, 700, 800, 900, 1000, or ranges including and/or spanning the aforementioned values.

In some embodiments, the weight percent of progesterone in the composition is equal to or greater than about: 1, 2, 5, 10, 20, 30, 40, 50, 60, or ranges including and/or spanning the aforementioned values.

In some embodiments, as disclosed elsewhere herein, the composition includes one or more glucocorticoids. In some embodiments, the composition comprises a glucocorticoid source. In some embodiments, the glucocorticoid source comprises precursors (e.g., prodrugs) of the glucocorticoid, the glucocorticoid itself, or mixtures of the foregoing. In some embodiments, the amount of the one or more glucocorticoids (individually or collectively) administered (in mg per day) is equal to or greater than about: 0.1, 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 750, 1000, 1250, 1500, 1750, 2000 or ranges including and/or spanning the aforementioned values. In some embodiments, the amount of glucocorticoid (individually or collectively) present (in mg) per dose is equal to or greater than about: 0.1, 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 750, 1000, 1250, 1500, 1750, 2000 or ranges including and/or spanning the aforementioned values. In some embodiments, the glucocorticoid may include one or more of hydrocortisone, prednisone, prednisolone, dexamethasone, cortisone, methylprednisolone, betamethasone, triamcinolone, fludrocortisone acetate, and/or deoxycorticosterone acetate. The structures of hydrocortisone and dexamethasone is shown in FIG. 3.

In some embodiments, the weight percent of one or more glucocorticoids (individually or collectively) in the composition is equal to or greater than about: 0, 1, 2, 5, 10, 20, 30, 40, 50, 60, or ranges including and/or spanning the aforementioned values.

In some embodiments, as disclosed elsewhere herein, the composition includes androgen. In some embodiments, the amount of androgen administered (in mg per day) is equal to or greater than about: 0.1, 1, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, or ranges including and/or spanning the aforementioned values. In some embodiments, the amount of androgen present (in mg) per dose is equal to or greater than about: 0.1, 1, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, or ranges including and/or spanning the aforementioned values.

In some embodiments, the weight percent of androgen in the composition is equal to or greater than about: 0, 1, 2, 5, 10, 20, 30, 40, 50, 60, or ranges including and/or spanning the aforementioned values.

In some embodiments, as disclosed elsewhere herein, the composition includes dexamethasone. In some embodiments, the amount of dexamethasone administered (in mg per day) is equal to or greater than about: 0.1, 1, 2, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, or ranges including and/or spanning the aforementioned values. In some embodiments, the amount of dexamethasone present (in mg) per dose is equal to or greater than about: 0.1, 1, 2, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, or ranges including and/or spanning the aforementioned values.

In some embodiments, the weight percent of dexamethasone in the composition is equal to or greater than about: 0, 1, 2, 5, 10, 20, 30, 40, 50, 60, or ranges including and/or spanning the aforementioned values.

In some embodiments, as disclosed elsewhere herein, the composition includes a lubricant. In some embodiments, the amount of the lubricant administered (in mg per day) is equal to or greater than about: 0.1, 1, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, or ranges including and/or spanning the aforementioned values. In some embodiments, the amount of the lubricant present (in mg) per dose is equal to or greater than about: 0.1, 1, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, or ranges including and/or spanning the aforementioned values.

In some embodiments, the weight percent of lubricant in the composition is equal to or greater than about: 0, 1, 2, 5, 10, 20, 30, 40, 50, 60, 70, 80 or ranges including and/or spanning the aforementioned values.

In some embodiments, as disclosed elsewhere herein, the composition includes a carrier. In some embodiments, the amount of the carrier administered (in mg per day) is equal to or greater than about: 0.1, 1, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, or ranges including and/or spanning the aforementioned values. In some embodiments, the amount of the carrier present (in mg) per dose is equal to or greater than about: 0.1, 1, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, or ranges including and/or spanning the aforementioned values.

In some embodiments, the weight percent of carrier in the composition is equal to or greater than about: 0, 1, 2, 5, 10, 20, 30, 40, 50, 60, 70, 80 or ranges including and/or spanning the aforementioned values.

As disclosed elsewhere herein, in some embodiments, the composition comprises a testosterone source, an aromatase inhibitor, and an estriol source. The testosterone source may be testosterone or an ester thereof. The estriol source may be estriol or an ester thereof. In some embodiments, the composition may comprise testosterone, an aromatase inhibitor, estriol, progesterone, and hydrocortisone. In some embodiments, the composition may further comprise phytoestrogen, vitamin D3, estrogen, a glucocorticoid, and one or more androgen. The one or more androgen may comprise dehydroepiandrosterone sulfate or androstenedione. The aromatase inhibitor may be selected from anastrozole, letrozole, exemestane, or a combination thereof. In some embodiments, the composition may also include a pharmaceutically acceptable excipient.

In some embodiments, the composition includes testosterone (10-500 mg per day and/or per dose, or as disclosed elsewhere herein), an aromatase inhibitor (10-500 mg per day and/or per dose, or as disclosed elsewhere herein), and estriol (10-500 mg per day and/or per dose, or as disclosed elsewhere herein). The compositions may have one or more of the aforementioned components in a range of quantities. The quantities vary depending on the circumstance, requirements, or purpose of the specific formulation. Thus, for example, one formulation may require a greater quantity of any one or more component than a different formulation. Thus, the provided quantities are given by way of example only and are not intended to be limiting in scope.

Each compound as described herein can be formulated alone pursuant to the teachings below. In some embodiments, active agents as disclosed herein may be administered in different compositions through alternative routes or through the same route. For instance, in some embodiments, multiple different compositions may be administered simultaneously, sequentially, or at different times through one or more routes. To illustrate, one composition may include testosterone and progesterone. Another composition may include an aromatase inhibitor. Those compositions may then be administered to the patient via the same route (e.g., topically) or by different routes (orally and topically). The compositions can be prepared for oral administration or can be combined, based on compatibility, for co-administration (e.g., of testosterone, an aromatase inhibitor, and estriol, etc.) in a single oral unit dosage form.

As disclosed elsewhere herein, in some embodiments, the composition comprises one or more non-active ingredients. In other embodiments, the non-active ingredients are configured to act as an inert carrier for the active ingredients. The composition may be formulated as a unit dose. In some embodiments, the composition comprises a form that is configured to be readily ingested by a human and/or animal subject. For example, the composition comprises a pill, pellet, or tablet. The composition may be formulated as a pellet. In other examples, the composition comprises a gel or a cream.

Methods of Treatment

Aspects disclosed herein relate to administering to a subject in need an effective amount of a composition comprising one or more of a testosterone source, an aromatase inhibitor, estriol, and/or other agents as disclosed elsewhere herein.

As disclosed elsewhere herein, some embodiments pertain to treating Alzheimer's disease through administration of a composition as disclosed herein. A subject in need of receiving a composition as disclosed herein to improve the subject's health need not always be identified prior to receiving a first treatment with the composition. For example, a subject may be predetermined that they will develop Alzheimer's disease prior to showing any signs of Alzheimer's disease. Alternatively, the subject may receive treatment prophylactically if he or she is at risk or not at risk of Alzheimer's disease (e.g., once a patient reaches an age of equal to or greater than 50, 60, 70, etc.). Accordingly, in some embodiments, the composition is administered to the subject after the subject receives an early stage diagnosis. In some embodiments, not every subject is a candidate for such administration and identification of treatment subjects may be desirable. It is understood that patient selection depends upon a number of factors within the skill of the ordinarily skilled physician. Thus, some embodiments disclosed herein further comprise identifying a subject as one that will benefit from administering an effective amount of at least one compound or composition to increase longevity, increase survival time, increase life span, or improve upon immunization. Subjects may be identified on the basis of physiological factors specific to the subject according to the subject's age, present medical condition, present medical treatment, prescribed medical treatment, or in some embodiments, the subject being diagnosed with Alzheimer's disease. In some embodiments, treatment of includes preventing, reducing, and/or slowing the accumulation of beta-amyloids, amyloid plaques, and/or tangles in tau proteins. Beta-amyloid is a leftover fragment of a larger protein. When these fragments cluster together, they appear to have a toxic effect on neurons and to disrupt cell-to-cell communication. These clusters form larger deposits called amyloid plaques, which also include other cellular debris. Tau proteins play a part in a neuron's internal support and transport system to carry nutrients and other essential materials. In Alzheimer's disease, tau proteins change shape and organize themselves into structures called neurofibrillary tangles. The tangles disrupt the transport system and are toxic to cells.

In some aspects, a method of treating, preventing, or ameliorating a brain disease by administering a composition as described herein. In some embodiments, the brain disease is dementia. Dementia is a broad category of brain disease that cause a long-term and often gradual decrease in the ability to think and remember that is severe enough to affect daily functioning. Symptoms associated with dementia include emotional problems, difficulties with language, and a decrease in motivation. In some embodiments, the method comprises testing a subject for a dementia risk factor and administering a composition as described herein. In some embodiments, testing a subject for a dementia risk factor include performing a brain scan, performing a brain biopsy, cognitive testing, and testing a subjects blood. Subjects may be identified on the basis of physiological factors specific to the subject according to the subject's age, present medical condition, present medical treatment, prescribed medical treatment, or in some embodiments, the subject being diagnosed with dementia. In some embodiments, the method further comprises administering one or more cholinesterase inhibitors. In some embodiments, the cholinesterase inhibitor is donepezil. In some embodiments, the method further comprises administering to the subject a MIND diet.

In some embodiments, a subject receives sufficient testosterone from multiple composition dosages before high levels of testosterone is achieved. One can readily and immediately envision a regimen wherein a subject is administered a first composition, and the subject receives one or more subsequent composition dosages. Such a regimen may continue such that the subject receives a third composition dosage after the subject receives the second composition dosage. In some embodiments, a subject may receive: 1, 2, 3, 4, 5, 6, 7, 8, 9, 10 or more doses during treatment. One or more additional hormones may be administered before the first composition dose, or before one or more subsequent composition dosages. In some embodiments, the subject receives doses over the time course of the remainder of his or her lifetime and/or over a period of years (e.g., greater than or equal to 1 year, 5 years, 10 years, 15 years, 20 years, 30 years, or ranges including and/or spanning the aforementioned values).

In some instances, a period of time passes between administering composition doses to a subject. In some embodiments, the time period between composition dosages is equal to or at least about: 1 day, 1 week, 2 weeks, 3 weeks, 1 month, 2 months, 3 months, 4 months, 5 months, 6 months, 7 months, 8 months, 9 months, 10 months, 11 months, 1 year, or ranges including and/or spanning the aforementioned values. In some embodiments, one or more additional hormones or therapeutic agents are administered to the subject during the period between the subject's administrations of the composition.

Some aspects provided herein provide for a method of producing supraphysiological high levels of testosterone in a subject. In some embodiments, the method includes providing a compound, composition, or combination as disclosed elsewhere herein to a subject. In some embodiments, the method comprises administering an effective amount of a composition as disclosed herein. In some embodiments, as disclosed herein, the composition comprises a testosterone source, an aromatase inhibitor, and estriol. In some embodiments, the composition further comprises progesterone. In some embodiments, the pharmaceutical composition further comprises a glucocorticoid. In some embodiments, the composition further comprises a pharmaceutical excipient. In some embodiments, the testosterone is not converted to estradiol in a subject.

In some embodiments, as discussed elsewhere herein, the subject is a human. However, the methods are not limited to the treatment of humans and are equally applicable to the treatment of mammals. In such instances of treating non-human mammals, patient selection depends upon a number of factors within the skill of the ordinarily skilled veterinarian or research scientist.

Some aspects provide a method of treating or ameliorating a disease, disorder, or condition associated with Alzheimer's Disease in a subject; the method comprising administering a therapeutically effective amount of a compound, composition, or combination as disclosed elsewhere herein to a subject. In some embodiments, the composition comprises testosterone, an aromatase inhibitor, and estriol. In some embodiments, the composition further comprises progesterone and a glucocorticoid. In some embodiments, the composition is configured to improve the subject's brain glucose metabolism. In some embodiments, the composition improves the subject's cerebral blood flow. In some embodiments, the composition prevents or inhibits the hyperphosphorylation of the tau protein. In some embodiments, the hyperphosphorylation of the tau protein is inhibited by equal to or at least about: 50%, 70%, 80%, 90%, 99%, or ranges including and/or spanning the aforementioned values. In some embodiments, the composition reduces β-amyloids in the subject's brain. In some embodiments, the β-amyloids in the subject's brain are reduced by equal to or at least about: 50%, 70%, 80%, 90%, 99%, or ranges including and/or spanning the aforementioned values.

In some embodiments, after administration of a compound, composition, or combination as disclosed elsewhere herein, the testosterone levels of a subject elevate by equal to or greater than about 10 ng/dL, 20 ng/dL, 30 ng/dL, 50 ng/dL, 90 ng/dL, 100 ng/dL, 120 ng/dL, 140 ng/dL, 160 ng/dL, 180 ng/dL, 190 ng/dL, 200 ng/dL, 210 ng/dL, 230 ng/dL, 240 ng/dL, 260 ng/dL, 270 ng/dL, 300 ng/dL, 320 ng/dL, 350 ng/dL, 360 ng/dL, 370 ng/dL, 380 ng/dL, 390 ng/dL, 400 ng/dL, 420 ng/dL, 430 ng/dL, 440 ng/dL, 460 ng/dL, 500 ng/dL, 600 ng/dL, 1000 ng/dL, 5000 ng/dL, or ranges including and/or spanning the aforementioned values. In some embodiments, after administration of a compound, composition, or combination as disclosed elsewhere herein, the bioavailable testosterone levels of a subject elevate by equal to or greater than about 10 ng/dL, 50 ng/dL, 100 ng/dL, 200 ng/dL, 400, ng/dL, 1000 ng/dL, 5000 ng/dL, or ranges including and/or spanning the aforementioned values. In some embodiments, the testosterone levels of a subject are raised by equal to or at least about: 10%, 20%, 40%, 60%, 80%, 100%, 120%, 140%, 160%, 180%, 3000% or ranges including and/or spanning the aforementioned values. In some embodiments, the levels of bioavailable testosterone are raised by equal to or at least about: 10%, 20%, 40%. 60%, 80%, 100%, 120%, 140%, 160%, 180%, 3000% or ranges including and/or spanning the aforementioned values.

In some embodiments, pharmaceutical composition is taken while the subject is on a MIND diet. The MIND (Mediterranean-DASH Intervention for Neurodegenerative Delay) diet refers to a hybrid of the Mediterranean-DASH diets. Example MIND diets may include, natural plant-based foods and limited intakes of animal and high saturated fat foods. In some MIND diets, the MIND diet comprises the consumption of berries and green leafy vegetables with low consumption of fruit, dairy, potato, or fish.

In some embodiments, before administration of a compound, composition, or combination as disclosed elsewhere herein, the subject's testosterone level is equal to or less than about: 350 ng/dL, 300 ng/dL, 250 ng/dL, 200 ng/dL, 150 ng/dL, 100 ng/dL, 50 ng/dL, or ranges including and/or spanning the aforementioned values. In some embodiments, after administration of a compound, composition, or combination as disclosed elsewhere herein, the subject's testosterone level is equal to or at least about: 350 ng/dL, 400 ng/dL, 450 ng/dL, 500 ng/dL, 550 ng/dL, 600 ng/dL, 650 ng/dL, 750 ng/dL, 1000 ng/dL, 1500 ng/dL, 5000 ng/dL, or ranges including and/or spanning the aforementioned values.

Some aspects provide a method of treating or ameliorating a disease in a subject, the method comprises administering an effective amount of a composition disclosed herein. In some embodiments, the disease is a cancer. The cancer may be breast cancer, ovarian cancer, or prostate cancer. In some embodiments, the disease is Parkinson's disease, type II diabetes, or metabolic syndrome. In some embodiments, the composition further comprises, at least one of, phytoestrogen, vitamin D3, progesterone, androgen, dehydroepiandrosterone sulfate, androstenedione, progestin, and a glucocorticoid. In some embodiments, the treating or ameliorating a disease is treating symptoms of the disease.

Some aspects provide a method for producing superphysiological free testosterone levels in a subject by administering an effective amount of a composition disclosed herein. In some embodiments, the subject is a male and the composition is configured to raise the subject's free testosterone level to equal to or greater than about 24 ng/dL, 30 ng/dL, 40 ng/dL, 50 ng/dL, 60 ng/dL, 100 ng/dL 200 ng/dL, 300 ng/dL, or ranges including and/or spanning the aforementioned values. In some embodiments, the subject is a female and the composition is configured to raise the subject's free testosterone level to equal to or greater than about 1 ng/dL, 2 ng/dL, 3 ng/dL, 4 ng/dL, 5 ng/dL, 6 ng/dL, 10 ng/dL 20 ng/dL, 30 ng/dL, or ranges including and/or spanning the aforementioned values.

In some embodiments, the composition downregulates β-secretase activity in a subject. In some embodiments, the β-secretase activity is reduced by equal to or at least about: 50%, 70%, 80%, 90%, 99%, or ranges including and/or spanning the aforementioned values. In some embodiments, the composition upregulates α-secretase activity in a subject. In some embodiments, the α-secretase activity is increased by equal to or at least about: 50%, 70%, 80%, 90%, 99%, or ranges including and/or spanning the aforementioned values. In some embodiments, the composition upregulates neprilysin activity in a subject. In some embodiments, the neprilysin activity is increased by equal to or at least about: 50%, 70%, 80%, 90%, 99%, or ranges including and/or spanning the aforementioned values.

Figure 4A:
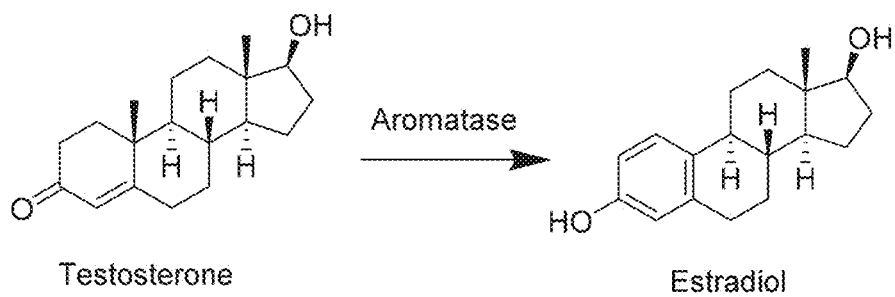
FIG. 4A is a scheme showing the conversion of testosterone to estradiol by aromatase.
Figure 4B:
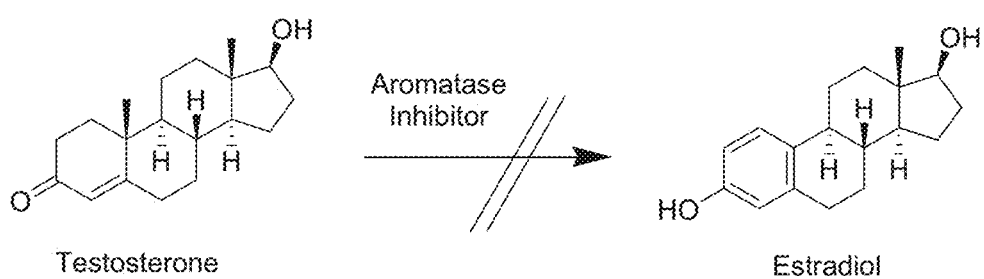
FIG. 4B is a scheme showing the blocking of conversion of testosterone to estradiol using an aromatase inhibitor.

As shown in FIG. 4A, testosterone can be converted to estradiol by aromatase enzymes. In some embodiments, the compositions as described herein prevent formation of the estradiol from the testosterone source. In some embodiments, the formation of estradiol is prevented using an aromatase inhibitor, as shown in FIG. 4B. In some embodiments, the amount of aromatase inhibitor is selected to inhibit the aromatase enzyme will depend on the condition of the subject. In some embodiments, the aromatase inhibitor is used in an amount that is effective in keeping estradiol blood serum levels less than about 54 pg/ml in males, less than 45 pg/ml in males, or less than 30 pg/ml in males. In some embodiments, the aromatase inhibitor is used in an amount that is effective in keeping estradiol blood serum levels less than about 30 pg/ml in females. Because the aromatase enzyme tends to reside in fat tissue, higher doses may be desirable in patients who are obese.

In accordance with one embodiment of the disclosure, a composition is provided that is able to (and/or configured to) provide nearly zero order release of the testosterone. In some embodiments, the composition is in excess of 90% or 98% of active agents and contains only a small amount of excipient. In some embodiments, the composition is an implant that is administered to the subject. In some embodiments, the implant contains a small amount of a pharmaceutically acceptable lubricant (such as stearic acid) sufficient to facilitate removal of the implant from the pellet forming mold without damage. In some embodiments, to improve the structural integrity of the pellet a small amount of a pharmaceutically acceptable binder is used (e.g., PVP (povidone) (0.2-2 mg) may be used).

A number of implant devices are known in the art that may be adopted for use in accordance with this disclosure. For example, H. Nash, et al., "Steroid Release From Silastic Capsules and Rods" Contraception, 18, 367-394 (1978), Shippy, et al., "Controlled Release of Testosterone Using Silicone Rubber" J. Biomed. Mater. Res., 7, 95-110 (1973), Japanese application JP 9044-310A, UK patent application 2,167,662, U.S. Pat. No. 3,948,254, U.K. Patent Appl. 2,154,138A, U.S. Pat. Nos. 5,035,891, and 10,071,104, all of which are herein incorporated by reference. In some embodiments, as disclosed herein, different routes of administration for active agents may be used, or the identical route may be used. For example, in several embodiments, a pellet may be used to provide all the active agents. In other embodiments, a pellet with some of the actives may be used in conjunction with another delivery system (e.g., a patch, etc.) to deliver other active ingredients.

As disclosed elsewhere herein, some embodiments also encompass methods for making and for administering the disclosed compositions. Multiple techniques of administering a compound (or compounds, composition, etc.) exist including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections. In some embodiments, administration is performed through oral pathways, which administration includes administration in capsule, tablet granule, pellet, spray, syrup, or other such forms. In some embodiments, the compounds (e.g., active agents) or composition is provided as a controlled release formulations or depot formulations (which may include a pellet). In some embodiments, the controlled release or depot formulation releases one or more active agents of the compositions disclosed herein over a period of equal to or at least about: 1 month, 2 months, 3 months, 6 months, a year, or ranges including and/or spanning the aforementioned values. As further examples of such modes of administration and as further disclosure of modes of administration, disclosed herein are various methods for administration of the disclosed compositions including modes of administration through intraocular, intranasal, and intraauricular pathways.

In some embodiments, compounds as disclosed herein may be administered simultaneously or sequentially. In some embodiments, where the compounds are not provided in the same composition (e.g., multiple separate compositions are provided to deliver the appropriate combination), the compositions may be administered via different routes (e.g., oral and intravenously, etc.). In other embodiments, the composition is administered to the subject concurrent with the subject receiving one or more additional therapeutic agents (e.g., approved Alzheimer's disease drugs or cancer drugs). In some embodiments, concurrent administration can be effected by multiple administrations within a limited period of time (for example, a single office visit with a physician) or concurrent administration can be effected simultaneously or near simultaneously.

In some embodiments, the compositions may be provided in a dosage form. The dosage form may be a capsule, a pellet, a pill or a tablet. In some embodiments, the dosage form is a pellet and the pellet is formed when the composition is molded and compressed into a standard pellet press using applied pressure. The applied pressure is from 400 pounds, 600 pounds, 1000 pounds, 1500 pounds, 2000 pounds, 3000 pounds, 4000 pounds, or ranges including and/or spanning the aforementioned values. In some embodiments, the pellet may be circular, cylindrical, square or rectangular. In a further embodiment, the pellet is cylindrical. In some embodiments, the cylindrical pellet may have a diameter from 2.0 millimeters (mm), 2.3 mm, 2.6 mm, 2.8 mm, 3.1 mm, 3.4 mm, 3.7 mm, 4.0 mm or ranges including and/or spanning the aforementioned values. In some embodiments, the pellet has a mass of 50 milligrams (mg), 75 mg, 80 mg, 85 mg, 90 mg, 95 mg, 100 mg, 105 mg, 120 mg, 140 mg, 145 mg, 150 mg, 155 mg, 200 mg, 250 mg, 290 mg, 300 mg, 310 mg, 400 mg, 500 mg, 600 mg, 1000 mg or ranges including and/or spanning the aforementioned values.

The compositions may, if desired, be presented in a pack or dispenser device which may contain one or more unit dosage forms containing the active ingredient. The pack may for example comprise metal or plastic foil, such as a blister pack. The dispenser device may be a sealed glass ampule. In some embodiments, the pack or dispenser device may be sterilized using gamma radiation. In some embodiments, the pack or dispenser device may be sterilized by being autoclaved at temperature and pressure greater than ambient. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

In aspects, administering a composition described herein may increase longevity, survival time, life span, or health span of the subject. In some embodiments, the expected longevity, survival time, life span, or health span of the subject is the median expectation for similarly situated subjects. In other embodiments, the expected longevity, survival time, life span, or health span of the subject is the mean expectation for similarly situated subjects. Subjects of similar situation may be determined based upon any one or more factors, including but not limited to, age, health, family history, or activity levels. In some embodiments, the expected increase as measured from the time treatment is started may be 1%, 2%, 3%, 4%, 5%, 6%, 7%, 8%, 9%, 10%, 11%, 12%, 13%, 14%, 15%, 16%, 17%, 18%, 19%, 20%, 21%. 22%, 23%, 24%, 25%, 26%, 27%, 28%, 29%, 30%. 40%, 50%, 1000%, about any of the aforementioned percentages, or a range bounded by any of the aforementioned percentages (e.g., about 1%-30%, about 5%-25%, about 5%-20%, about 5%-15% or 1%-30%, 5%-25%, 5%-20%, 5%-15%), 1%-100%, 1%-90%, 1%-80%, 1%-70%, 1%-60%, 1%-50%, 1%-40%, 1%-30%, 1%-20%, 1%-10%, 10%-100%, 10%-90%, 10%-80%, 10%-70%, 10%-70%, 10%-60%, 10%-50%, 10%-40%, 10%-30%, 10%-20%, 20%-100%, 20%-90%, 20%-80%, 20%-70%, 20%-60%, 20%-50%, 20%-40%, 20%-30%, 30%-100%, 30%-90%, 30%-80%, 30%-70%, 30%-60%,30%-50%, 30%-40%, 40%-100%, 40%-90%, 40%-80%, 40%-70%, 40%-60%, 40%-50%, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, 90%-1000%, about any of the aforementioned range of percentages (e.g., about 10%-70%, about 30%-60%, or about 50%-70%), relative to the expected longevity, survival time, life span, or health span of the subject. In some embodiments, the expected increase is in years and is 1-40 years, 1-19 years, 1-18 years, 1-17 years, 1-16 years, 1-15 years, 1-14 years, 1-13 years, 1-12 years, 1-11 years, 1-10 years, 1-9 years, 1-8 years, 1-7 years, 1-6 years, 1-5 years, 1-4 years, 1-3 years, 1-2 years, 1 year, at least the aforementioned years (e.g., at least 1-10 years), or about the aforementioned years (e.g., about 1-2 years or at least about 1-2 years), relative to the expected longevity, survival time, life span, or health span of the subject. In some embodiments the expected increase is in days to months, and is one day to one year, one day to 11 months, one day to 10 months, one day to 9 months, one day to 8 months, one day to 7 months, one day to 6 months, one day to 5 months, one day to 4 months, one day to 3 months, one day to 2 months, one day to one month, at least the aforementioned range of days to months (e.g., at least one day to 11 months), or about the aforementioned range of days to months (e.g., about one day to 6 months or at least about one day to 6 months), relative to the expected longevity, survival time, life span, or health span of the subject.

Some embodiments pertain to a method of treating and/or preventing Alzheimer's disease. In some embodiments, the method comprises administering to a subject in need of treatment the composition as described elsewhere herein. In some embodiments, the subject's β-amyloid. 42/β-amyloid 40 ratio is lowered. In some embodiments, the composition improves the subject's brain glucose metabolism. In some embodiments, the composition improves the subject's cerebral blood flow. In some embodiments, the composition prevents or substantially prevents the hyperphosphorylation of the tau protein. In some embodiments, the composition reduces β-amyloids the subject's brain. In some embodiments, the composition reduces cardiac arrest and stroke in a subject.

Combination Therapies

As disclosed elsewhere herein, some embodiments provide for coadministering a composition described herein with an additional therapeutic agent. In some embodiments, the additional therapeutic agent may comprise cholinesterase inhibitors such as donepezil, galantamine, rivastigmine, memantine; managing behavior, such as citalopram, mirtazapine, sertraline, bupropion, duloxetine, imipramine; sleep aids, such as zolpidem, eszopiclone, zaleplon, antianxiety, such as lorazepam, clonazepam; anticonvulsants, such as sodium valproate, carbamazepine, oxcarbazepine; antipsychotics such as risperidone, quetiapine, olanzapine can be employed.

Combination therapies can include fixed combinations, in which two or more pharmaceutically active agents are in the same formulation; kits, in which two or more pharmaceutically active agents in separate formulations are sold in the same package, e.g., with instructions for co-administration; and free combinations in which the pharmaceutically active agents are packaged separately, but instruction for simultaneous or sequential administration are provided. Other kit components can include diagnostics, assays, multiple dosage forms for sequential or simultaneous administration, instructions and materials for reconstituting a lyophilized or concentrated form of the pharmaceutical composition, apparatus for administering the pharmaceutically active agents, and the like. For example, a pharmaceutical package is provided comprising a first drug substance which is a compound of embodiments disclosed elsewhere herein and at least one second drug substance, along with instructions for combined administration. A pharmaceutical package is also provided comprising a compound of embodiments disclosed elsewhere herein along with instructions for combined administration with at least one second drug substance. Also provided is a pharmaceutical package comprising at least one second drug substance along with instructions for combined administration with a compound of the present disclosure.

Treatment with combinations according to embodiments disclosed elsewhere herein may provide improvements or superior outcome compared with treatments by either component of the combination alone. For example, a pharmaceutical combination comprising an amount of a compound of some embodiments and an amount of a second drug substance can be employed, wherein the amounts are appropriate to produce a synergistic therapeutic effect. In some embodiments, a pharmaceutical combination comprising a testosterone source, an estriol source, and an aromatase inhibitor produces a synergistic therapeutic effect over a combination comprising any two of the foregoing components. In some embodiments, a pharmaceutical combination comprising a testosterone source, an estriol source, and a glucocorticoid produces a synergistic therapeutic effect over a combination comprising any two of the foregoing components. In some embodiments, a pharmaceutical combination comprising a testosterone source, an estriol source, and a progesterone source produces a synergistic therapeutic effect over a combination comprising any two of the foregoing components. In some embodiments, a pharmaceutical combination comprising a testosterone source, an estriol source, a glucocorticoid, and an aromatase inhibitor produces a synergistic therapeutic effect over a combination comprising any two of the foregoing components. In some embodiments, a pharmaceutical combination comprising a testosterone source, an estriol source, a glucocorticoid, progesterone and an aromatase inhibitor produces a synergistic therapeutic effect over a combination comprising any two of the foregoing components. In some embodiments, a pharmaceutical combination comprising a testosterone source, an estriol source, a glucocorticoid, and an aromatase inhibitor produces a synergistic therapeutic effect over a combination comprising any two of the foregoing components. In some embodiments, a pharmaceutical combination comprising a testosterone source, an estriol source, a glucocorticoid, progesterone, phytoestrogen, and an aromatase inhibitor produces a synergistic therapeutic effect over a combination comprising any two of the foregoing components. In some embodiments, a pharmaceutical combination comprising a testosterone source, an estriol source, a glucocorticoid, one or more androgens, progesterone, phytoestrogen, and an aromatase inhibitor produces a synergistic therapeutic effect over a combination comprising any two of the foregoing components. In some embodiments, a pharmaceutical combination comprising a testosterone source, an estriol source, one or more androgens, and an aromatase inhibitor produces a synergistic therapeutic effect over a combination comprising any two of the foregoing components. A method for improving the therapeutic utility of a compound of some embodiments is also provided, comprising co-administering, e.g., concomitantly or in sequence, a therapeutically effective amount of a compound of some embodiments and a second therapeutic substance. A method for improving the therapeutic utility of a second substance is also provided comprising co-administering, e.g., concomitantly or in sequence, a therapeutically effective amount of a compound of some embodiments and a second drug substance. A combination of some embodiments disclosed herein and a second therapeutic substance as a combination partner can be administered by any conventional route, for example as set out above for a compound of some embodiments. A second drug can be administered in dosages as appropriate, e.g., in dosage ranges which are similar to those used for single treatment, or, e.g., in case of synergy, even below conventional dosage ranges.

In some embodiments, the compounds and/or agents as disclosed herein can generally be employed as the free acid or the free base. Alternatively, the compounds may be in the form of acid or base addition salts. The term "pharmaceutically acceptable salt" of compounds of some embodiments is intended to encompass any and all acceptable salt forms.

While salt forms of some embodiments are preferably pharmaceutically acceptable salts, in certain embodiments pharmaceutically unacceptable salts can be employed (e.g., for preparation, isolation, and/or purification purposes). The compounds of preferred embodiments can also be employed in the form of a solvate, or in various combinations of forms (free acid, free base, salt, and/or solvate). A compound of some embodiments in free form can be converted into a corresponding compound in the form of a salt; and vice versa. A solvate of a compound in free form or in the form of a salt can be converted into a corresponding non-solvate form of the compound in free form or in the form of a salt, and vice versa.

Dosing Regimes

The dosage of active ingredient(s) may range broadly, depending upon the desired affects and the therapeutic indication. Typically, dosages of active ingredient(s) may be between about 10 microgram/kg and 100 mg/kg body weight per dose, between about 100 microgram/kg and 10 mg/kg body weight per dose, or ranges including and/or spanning the aforementioned values. Alternatively dosages may be based and calculated upon the surface area of the patient, as understood by those of skill in the art. Administration is may be oral on a daily or twice daily basis. Administration may include four tablets taken by mouth daily, in some embodiments, tablets may be administered during a meal time. In some embodiments, two tablets may be administered during a meal. In some embodiments, two tablets may be administered at breakfast and two at lunch.

The exact formulation, route of administration and dosage can be chosen in view of the consumer's condition. See for example, Fingl et al., in The Pharmacological Basis of Therapeutics, 1975, which is incorporated herein by reference in its entirety. The magnitude of an administrated dose may vary with the severity of a particular medical or physical condition and the route of administration. The severity of a condition may, for example, be evaluated, in part, by standard prognostic evaluation methods. Further, the dose and perhaps dose frequency may also vary according to the age, body weight, and response of the individual. A program comparable to that discussed above may be used in veterinary medicine.

In some embodiments, the pharmaceutical composition (e.g., a dose of the pharmaceutical composition) is administered once per day, twice per day, three times per day, four times per day, or more than four times per day. In some embodiments, the pharmaceutical composition is administered once per day, twice per day, three times per day, four times per day, or more than four times per cycle of treatment. In some embodiments, the pharmaceutical composition is administered at the intervals described elsewhere herein.

Pharmaceutical Compositions

Also, as disclosed elsewhere herein, provided herein are pharmaceutical compositions for the methods provided herein. In some embodiments, the pharmaceutical compositions comprise one or more of a testosterone source, an aromatase inhibitor, estriol, other active agents as disclosed herein, and a pharmaceutically acceptable carrier. The pharmaceutical compositions disclosed herein may be manufactured by means of conventional mixing, dissolving, granulating, dragee-making, levigating, emulsifying, encapsulating, entrapping or tableting processes, and/or pelleting processes. Additionally, the compounds are contained in an amount effective to achieve its intended purpose. Many of the compounds used in the pharmaceutical combinations disclosed herein may be provided as salts with pharmaceutically compatible counter ions.

Compounds, or mixtures of compounds described herein, can be synthetic, naturally-occurring, or a combination thereof. Compounds, or mixtures of compounds described herein may comprise testosterone, an aromatase inhibitor, and estriol. Compounds, or mixtures of compounds described herein, can be formulated into pharmaceutical composition comprising a pharmaceutically acceptable carrier and other excipients as apparent to the skilled worker. Such composition can additionally contain effective amounts of other compounds, especially for the treatment of conditions, diseases, and/or disorders described herein.

One or more of the compounds can be provided in the form of pharmaceutically acceptable salts, active metabolites, or tautomers thereof. Some embodiments can be provided in pharmaceutical compositions comprising a therapeutically effective amount of the compound. In some embodiments, the pharmaceutical composition also contains at least one pharmaceutically acceptable inactive ingredient. The composition can be formulated for intravenous injection, subcutaneous injection, oral administration, buccal administration, inhalation, nasal administration, topical administration, transdermal administration, ophthalmic administration, or optic administration. The pharmaceutical composition can be in the form of a tablet, a pill, a capsule, a liquid, an inhalant, a nasal spray solution, a suppository, a suspension, a gel, a colloid, a dispersion, a solution, an emulsion, an ointment, a lotion, an eye drop, or an ear drop.

In some embodiments, the compositions and preparations described contain one ore more active agents as disclosed herein (e.g., one or more of a testosterone source, an estriol source, a progesterone source, an aromatase inhibitor, a glucocorticoid, etc.). In some embodiments, the composition comprises a carrier. In some embodiments, the composition comprises a diluent. In some embodiments, the composition comprises an excipient.

In some embodiments, the compositions and preparations described contain at least 0.1% of active agent. The percentage of the compositions and preparations can, of course, be varied, and can contain between about 2% and 90% of the weight of the amount administered or ranges including and/or spanning the aforementioned values. In some embodiments, the percentage of the compositions and preparations can contain between about 2, 5, 10, or 15% and 30, 35, 40, 45, 50, 55, 60, 65, 70, 75, 80, 85, 90%, or any value in between, of the weight of the amount administered. The amount of active compounds in such pharmaceutically useful compositions and preparations is such that a suitable dosage will be obtained.

The active agents can form salts, which are also within the scope of some embodiments. Reference to a compound of the active agent herein is understood to include reference to salts thereof, unless otherwise indicated. The term "salt(s)", as employed herein, denotes acidic and/or basic salts formed with inorganic and/or organic acids and bases. In addition, when an active agent contains both a basic moiety, such as, but not limited to an amine or a pyridine or imidazole ring, and an acidic moiety, such as, but not limited to a carboxylic acid, zwitterions ("inner salts") can be formed and are included within the term "salt(s)" as used herein. Pharmaceutically acceptable (e.g., non-toxic, physiologically acceptable) salts can be used, although other salts are also useful, e.g., in isolation or purification steps, which can be employed during preparation. Salts of the compounds of the active agent can be formed, for example, by reacting a compound of the active agent with an amount of acid or base, such as an equivalent amount, in a medium such as one in which the salt precipitates or in an aqueous medium followed by lyophilization.

When the compounds according to some embodiments are in the forms of salts, they may be pharmaceutically acceptable salts. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Examples of metal salts include lithium, sodium, potassium, magnesium salts and the like. Examples of ammonium and alkylated ammonium salts include ammonium, methylammonium, dimethylammonium, trimethyammonium, ethylammonium, hydroxyethylammonium, diethylammonium, butylammonium, tetramethylammonium salts and the like. Examples of organic bases include lysine, arginine, guanidine, diethanolamine, choline and the like.

It is understood that the methods and combinations described herein include crystalline forms (also known as polymorphs, which include the different crystal packing arrangements of the same elemental composition of a compound), amorphous phases, esters, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Prodrugs (e.g., precursors to a drug molecule) and solvates of the compounds of the embodiments are also contemplated herein. The term "prodrug", as employed herein, denotes a compound which, upon administration to a subject, undergoes chemical conversion by metabolic or chemical processes to yield a compound of the active agent, and/or a salt and/or solvate thereof.

Compositions of the present disclosure can be prepared by blending with a pharmaceutically acceptable oil; generally, the oil comprises at least one medium chain fatty acid such as medium chain fatty acids comprising at least one mono-, di-, or triglyceride, or derivative thereof, or combinations thereof. Optionally added are other excipients including, for example and without limitation, anti-oxidants, lubricants and the like. Sufficient oil is used to form a suspension of micronized hormones or, in the alternative, solubilized hormones.

The compound(s) can be in admixture with a suitable carrier, diluent, or excipient such as sterile water, physiological saline, glucose, or the like, and can contain auxiliary substances such as wetting or emulsifying agents, pH buffering agents, gelling or viscosity enhancing additives, preservatives, flavoring agents, colors, and the like, depending upon the route of administration and the preparation desired. See, e.g., "Remington: The Science and Practice of Pharmacy", Lippincott Williams & Wilkins; 20th edition (Jun. 1, 2003) and "Remington's Pharmaceutical Sciences," Mack Pub. Co.; $18^{th}$ and $19^{th}$ editions (December 1985, and June 1990, respectively). Such preparations can include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroplasts. Suitable lipids for liposomal formulation include, without limitation, monoglycerides, diglycerides, sulfatides, lysolecithin, phospholipids, saponin, bile acids, and the like. The presence of such additional components can influence the physical state, solubility, stability, rate of in vivo release, and rate of in vivo clearance, and are thus chosen according to the intended application, such that the characteristics of the carrier are tailored to the selected route of administration.

Suitable inert materials include diluents, such as carbohydrates, mannitol, lactose, anhydrous lactose, cellulose, sucrose, modified dextrans, starch, and the like, or inorganic salts such as calcium triphosphate, calcium phosphate, sodium phosphate, calcium carbonate, sodium carbonate, magnesium carbonate, and sodium chloride. Disintegrants or granulating agents can be included in the formulation, for example, starches such as corn starch, alginic acid, sodium starch glycolate, Amberlite, sodium carboxymethylcellulose, ultramylopectin, sodium alginate, gelatin, orange peel, acid carboxymethyl cellulose, natural sponge and bentonite, insoluble cationic exchange resins, powdered gums such as agar, karaya or tragacanth, or alginic acid or salts thereof.

Binders can be used to form a hard tablet. Binders include materials from natural products such as acacia, tragacanth, starch and gelatin, methyl cellulose, ethyl cellulose, carboxymethyl cellulose, polyvinyl pyrrolidone, hydroxypropylmethyl cellulose, and the like.

Lubricants, such as stearic acid or magnesium or calcium salts thereof, polytetrafluoroethylene, liquid paraffin, vegetable oils and waxes, sodium lauryl sulfate, magnesium lauryl sulfate, polyethylene glycol, starch, talc, pyrogenic silica, hydrated silicoaluminate, and the like, can be included in tablet formulations.

Controlled release formulations can be employed wherein the amifostine or analog(s) thereof is incorporated into an inert matrix that permits release by either diffusion or leaching mechanisms. Slowly degenerating matrices can also be incorporated into the formulation. Other delivery systems can include timed release, delayed release, or sustained release delivery systems.

Coatings can be used, for example, nonenteric materials such as methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols, or enteric materials such as phthalic acid esters. Dyestuffs or pigments can be added for identification or to characterize different combinations of active compound doses The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, and salicylic acid. Pharmaceutical compositions will generally be tailored to the specific intended route of administration.

The pharmaceutical compositions described herein can be administered to a human patient per se, or in pharmaceutical compositions where they are mixed with other active ingredients, as in combination therapy, or excipients, or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound, salt and/or composition exist in the art including, but not limited to, oral, rectal, pulmonary, topical, aerosol, injection, infusion and parenteral delivery, including intramuscular, subcutaneous, intravenous, intramedullary injections, intrathecal, direct intraventricular, intraperitoneal, intranasal and intraocular injections. In some embodiments, the compositions described herein or a pharmaceutically acceptable salt of any of the foregoing, can be administered orally or intravenously.

For oral administration, the pharmaceutical compositions can be provided as a tablet, aqueous or oil suspension, dispersible powder or granule, emulsion, hard or soft capsule, syrup or elixir. Compositions intended for oral use can be prepared according to any method known in the art for the manufacture of pharmaceutical compositions and can include one or more of the following agents: sweeteners, flavoring agents, coloring agents and preservatives. Aqueous suspensions can contain the active ingredient in admixture with excipients suitable for the manufacture of aqueous suspensions.

Formulations for oral use can also be provided as hard gelatin capsules, wherein the active ingredient(s) are mixed with an inert solid diluent, such as calcium carbonate, calcium phosphate, or kaolin, or as soft gelatin capsules. In soft capsules, the active compounds can be dissolved or suspended in suitable liquids, such as water or an oil medium, such as peanut oil, olive oil, fatty oils, liquid paraffin, or liquid polyethylene glycols. Stabilizers and microspheres formulated for oral administration can also be used. Capsules can include push-fit capsules made of gelatin, as well as soft, sealed capsules made of gelatin and a plasticizer, such as glycerol or sorbitol. The push-fit capsules can contain the active ingredient in admixture with fillers such as lactose, binders such as starches, and/or lubricants such as talc or magnesium stearate and, optionally, stabilizers. In instances where it is desirable to maintain a compound in a reduced form (in the case of certain active metabolites), it can be desirable to include a reducing agent in the capsule or other dosage form.

Tablets can be uncoated or coated by known methods to delay disintegration and absorption in the gastrointestinal tract and thereby provide a sustained action over a longer period of time.

Kits

The compounds of some embodiments can be provided to an administering physician or other health care professional in the form of a kit. The kit is a package which houses a container which contains the compound(s) in a suitable pharmaceutical composition, and instructions for administering the pharmaceutical composition to a subject. The kit can optionally also contain one or more additional therapeutic agents. For example, a kit containing one or more compositions comprising compound(s) of some embodiments in combination with one or more additional therapeutic agent can be provided, or separate pharmaceutical compositions containing a compound of some embodiments and additional therapeutic agents can be provided. The kit can also contain separate doses of a compound of some embodiments for serial or sequential administration. The kit can optionally contain one or more diagnostic tools and instructions for use. The kit can contain suitable delivery devices, e.g., syringes, and the like, along with instructions for administering the compound(s) and any other therapeutic agent. The kit can optionally contain instructions for storage, reconstitution (if applicable), and administration of any or all therapeutic agents included. The kits can include a plurality of containers reflecting the number of administrations to be given to a subject. In some embodiments, a kit for the treatment of Alzheimer's disease is provided that includes the compositions described herein or another formulation and one or more therapeutic agent currently employed for the treatment of Alzheimer's disease. For example, cholinesterase inhibitors such as donepezil, galantamine, rivastigmine, memantine; managing behavior, such as citalopram, mirtazapine, sertraline, bupropion, duloxetine, imipramine; sleep aids, such as zolpidem, eszopiclone, zaleplon; anti-anxiety, such as lorazepam, clonazepam; anticonvulsants, such as sodium valproate, carbamazepine, oxcarbazepine; antipsychotics such as risperidone, quetiapine, olanzapine can be employed.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The above description discloses several methods and materials of the present disclosure. This disclosure is susceptible to modifications in the methods and materials, as well as alterations in the fabrication methods and equipment. Such modifications will become apparent to those skilled in the art from a consideration of this disclosure or practice of the disclosure disclosed herein. Consequently, it is not intended that this disclosure be limited to the specific embodiments disclosed herein, but that it cover all modifications and alternatives coming within the true scope and spirit of the disclosure.

EXAMPLES

The following examples are given for the purpose of illustrating various embodiments of the disclosure and are not meant to limit the present disclosure in any fashion. One skilled in the art will appreciate readily that the present disclosure is well adapted to carry out the objects and obtain the ends and advantages mentioned, as well as those objects, ends and advantages inherent herein. Changes therein and other uses which are encompassed within the spirit of the disclosure as defined by the scope of the claims will occur to those skilled in the art.

Example 1

This example describes results from the treatment of a 71 year old male patient who was referred for testosterone therapy. The patient was diagnosed with dementia and memory related issues. There was a strong family history of AD in his mother and maternal aunt. He presented with complaints of memory loss and lack of concentration. The patient had been diagnosed with dementia and mild cognitive impairment. The patient's wife reported no change or results with the Exelon® patch (rivastigmine).

Since 2014 the patient has been treated with increasing doses of testosterone with an aromatase inhibitor (anastrozole). This treatment, surprisingly, prevented significant progression of memory loss or cognitive changes for a period of several years. The patient was also maintained on an accelerated schedule of insertion of the hormone pellet. If the patient went past 12 weeks without treatment (e.g., insertion of the hormone pellet), be showed a significant decline in memory and function noticeable by his entire family.

In February of 2017, the patient presented mild cognitive impairment (on testing) that had remained stable since starting treatment. Clinical evaluation of the patient was performed, including nuclear medicine (NM) Pet Brain plaque imaging. Results of the testing showed a positive brain amyvid-PET scan. Significant cortical uptake suggested abnormal amyloid accumulation. The patient's results were diagnostic of AD, but, through treatment, the patient's symptoms had remained stable and had not progressed clinically.

Until recently (after 6 years on therapy), the patient remained entirely functional, working his farm and driving until the end of the pellet cycle. At the end of each pellet cycle, the patient experienced 'severe' memory loss. The wife noticed only gradual deterioration over the past year, though the patient is still functional. The patient no longer runs heavy equipment, but knows all his relatives (until the end of the cycle), and drives locally only. The patient's initial T level was 376 ng/dL with low free T (3.7 pg/ml). Patient's initial weight was 158 pounds.

TABLE 1

| Date | Testosterone dose (mg) | Anastrozole dose (mg) | Progesterone Hydrocortisone Dexamethasone Finasteride Dose (mg) | Lab Notes |
| --- | --- | --- | --- | --- |
| May 20, 2014 | 1680 | 12 | | |
| Sep. 18, 2014 | 1780 | 12 | | |
| Jan. 7, 2015 | 1780 | 12 | | |

TABLE 1-continued

| Date | Testosterone dose (mg) | Anastrozole dose (mg) | Progesterone Hydrocortisone Dexamethasone Finasteride Dose (mg) | Lab Notes |
|---|---|---|---|---|
| May 7, 2015 | 1980 | 12 | | |
| Jul. 30, 2015 | 2040 | 16 | | Helps a lot, unbelievably more alert |
| Nov. 9, 2015 | 2240 | 16 | | |
| Mar. 8, 2016 | 2240 | 16 | HC 400 | Not sure helped arthritis |
| May 31, 2016 | 2320 | 8 | | |
| Aug. 18, 2016 | 2320 | 8 | 24 F (GU symptoms) | Wt 164 End labs T > 1500 E2 53.7 |
| Oct. 25, 2016 | 2080 | 16 | | Brain function stable. Early return traveling |
| Jan. 24, 2017 | 2480 | 16 | 24F (Urinary SXS) | Feels like 'old self' |
| Apr. 28, 2017 | 2180 | 16 | 24F, 440 HC | Resume HC for arthritis pain Sign decline memory at end T > 1500 end, E2 49.6 |
| Jul. 26, 2017 | 2680 | 16 | 24F, 440 RC | |
| Oct. 25, 2017 | 2680 | 16 | 24E, 440 HC | |
| Dec. 26, 2017 | 2680 | 16 | 24F, 440 HC | |
| Feb. 20, 2018 | 7600 | 24 | 24F, 440 HC, P180 | c/o anxiety, E2 elevated past add P. A&O x4 |
| Apr. 24, 2018 | 2560 | 24 | 440 HC | Memory worse |
| Jun. 12, 2018 | 2560 | 24 | HC 400 | |
| Aug. 16, 2018 | 2560 | 24 | P200, RC 400 | Memory worse, read Prog. Increased dose of Wellbutrin for anxiety. Wife warned of cognitive side effects |
| Oct. 16, 2018 | 2560 | 24 | P200, ITC 400 | Every 8 weeks Helps memory T > 1500 E2 42.1 |
| Dec. 20, 2018 | 2680 | 32 | P200, RC 400 | |
| Feb. 21, 2019 | 2680 | 32 | P200, RC 440 | Short term memory at end |
| Apr. 10, 2019 | 2680 | 32 | P200 HC 450 | |
| Jun. 6, 2019 | 2680 | 37 | P380 HC 450 | Memory end |
| Aug. 26, 2019 | 2680 | 37 | P380 HC 450 | |
| Oct. 21, 2019 | 2680 | 32 | P380 HC 450 | |
| Dec. 18, 2019 | 7640 | 32 | P380 DMX 24 | Sleep apnea dx 12/19 Memory end. No overall progression |
| Feb. 12, 2020 | 2600 | 32 | P400, DMX 20 | |
| Apr. 27, 2020 | 7600 | 24 | P600, DMX 40 | Increase P to wean Zoloft EXPELLED PELLETS |
| Jun. 15, 2020 | 2600 | 24 | P600, DMX 40 | Memory worse overall, but pellets help |
| Aug. 12, 2020 | 2600 | 24 | P600, DMX 40 | Memory much worse at end |

Example 2

United States Pharmacopeia (USP) testosterone (10-99.5% of the total mass of the composition), a LISP aromatase inhibitor (0.5-50% of the total mass of the composition), a USP estriol source (0-60% of the total mass of the composition) and a USP glucocorticoid (0-50% of the total mass of the composition) are mixed with a carrier (0-80% of the total mass of the composition). The mixed composition is molded and compressed into a standard pellet press using 2000 pounds of pressure to form cylindrical pellets having a diameter of 3.1 mm and a mass of 100-600 mg.

The individual pellets are placed into sealed glass ampules or standard pharmaceutical blister packs. The ampules or blister packs are sterilized using gamma radiation or autoclaved at 121° C. for 40 minutes, steam generator pressure 20-25 psi, autoclave jacket pressure 5-25 psi.

Example 3

USP testosterone (30-99.5% of the total mass of the composition), USP anastrozole (2-30% of the total mass of the composition), USP estriol (0.5-20% of the total mass of the composition) and hydrocortisone (0.5-30% of the total mass of the composition) are mixed with dimethyl sulfoxide (DMSO) (0-20% of the total mass of the composition). The mixed composition is molded and compressed using the procedure described in Example 2 to form cylindrical pellets having a diameter of 3.1 mm and a mass of 290-310 mg. The pellets are packaged and sterilized using the procedure described in Example 2.

Example 4

USP testosterone (50-99.5% of the total mass of the composition), USP anastrozole (2-30% of the total mass of the composition), USP estriol (0.5-20% of the total mass of the composition) and hydrocortisone (0.5-30% of the total mass of the composition) are mixed with dimethyl sulfoxide (DMSO) (0-20% of the total mass of the composition). The mixed composition is molded and compressed using the procedure described in Example 2 to form cylindrical pellets having a diameter of 3.1 mm and a mass of 145-155 mg. The pellets are packaged and sterilized using the procedure described in Example 2.

Example 5

USP testosterone having a mass from 1500-3000 mg, USP anastrozole having a mass from 10-40 mg, USP estriol having a mass from 5-20 mg and hydrocortisone having a mass from 5-20 mg are mixed with stearic acid having a mass from 10-30 mg. The mixed composition is molded and compressed using the procedure described in Example 2 to form cylindrical pellets having a diameter of 3.1 mm and a mass of 75-85 mg. The pellets are packaged and sterilized using the procedure described in Example 2.

Example 6

USP testosterone (50-99.5% of the total mass of the composition), USP anastrozole (2-30% of the total mass of the composition). USP estriol (2-20% of the total mass of the composition), USP hydrocortisone (2-30% of the total mass of the composition), USP progesterone (2-30% of the total mass of the composition) and USP dexamethasone (2-30% of the total mass of the composition) are mixed with dimethyl sulfoxide (DMSO) (0-20% of the total mass of the composition). The mixed composition is molded and compressed using the procedure described in Example 2 to form cylindrical pellets having a diameter of 3.1 mm and a mass of 145-155 mg. The pellets are packaged and sterilized using the procedure described in Example 2.

Example 7

USP testosterone having a mass from 1680-2680 mg, USP anastrozole having a mass from 12-32 mg, USP estriol having a mass from 5-20 mg, USP hydrocortisone having a mass from 5-20 mg, USP progesterone having a mass from 2-20 mg and USP dexamethasone having a mass from 2-20 mg are mixed with stearic acid having a mass from 10-30 mg. The mixed composition is molded and compressed using the procedure described in Example 2 to form cylindrical pellets having a diameter of 3.1 mm and a mass of 75-85 mg. The pellets are packaged and sterilized using the procedure described in Example 2.

Example 8

This is a prophetic example. Participants aged 60 years or more who are at risk for AD are recruited. Thirty male participants are split into a group of 24 experimental subjects and 6 control subjects. Twenty female participants are split into a group of 15 experimental subjects and 5 control subjects. The experimental group receives subcutaneous testosterone replacement therapy (S-TRT). The control group receives a placebo. Two pellets produced as described in Example 5 are implanted into the subcutaneous tissue of the male experimental subjects once per week for four weeks. Two pellets produced as described in Example 7 are implanted into the subcutaneous tissue of the female experimental subjects once per week for four weeks. Two pellets containing magnesium stearate are implanted into the subcutaneous tissue of the control subjects once per week for four weeks. Serum levels of free testosterone and estradiol are measured before S-TRT is administered and at one-week intervals thereafter. Results for the male participants and the female participants are displayed in Table 2 and Table 3, respectively. For the experimental group after four weeks of S-TRT, free testosterone levels increased and estradiol levels generally are unaffected.

For the experimental group after ten years of S-TRT once per week, 96% of the experimental do not develop AD. Over the same period, in the placebo group, only 30% do not develop AD. Additionally, the longevity, life span, and health span of the experimental group is improved relative to the control group since the start of the study by 30%, 28%, and 50%, respectively. After death of any individuals in the study, the brain tissue of those subjects is analyzed. It is noted that the β-amyloid proteins in the experimental group is significantly less than for the placebo group.

TABLE 2

| Subject | Treatment | Initial Free T (ng/dL) | Initial Estradiol (ng/dL) | 4-week Free T (ng/dL) | 4-week Estradiol (ng/dL) |
|---|---|---|---|---|---|
| 1 | S-TRT | 850 | 11 | 1120 | 13 |
| 2 | S-TRT | 910 | 16 | 1300 | 17 |
| 3 | S-TRT | 880 | 29 | 910 | 32 |
| 4 | S-TRT | 960 | 10 | 980 | 11 |
| 5 | S-TRT | 730 | 12 | 1030 | 12 |
| 6 | S-TRT | 710 | 14 | 1310 | 15 |
| 7 | S-TRT | 760 | 22 | 1150 | 22 |
| 8 | S-TRT | 810 | 8 | 1310 | 9 |
| 9 | S-TRT | 910 | 14 | 1300 | 14 |
| 10 | S-TRT | 800 | 26 | 1040 | 28 |
| 11 | S-TRT | 760 | 30 | 1200 | 32 |
| 12 | S-TRT | 890 | 16 | 1150 | 18 |
| 13 | S-TRT | 990 | 12 | 1260 | 12 |
| 14 | S-TRT | 630 | 77 | 1010 | 24 |
| 15 | S-TRT | 710 | 15 | 1140 | 16 |
| 16 | S-TRT | 650 | 13 | 1070 | 14 |
| 17 | S-TRT | 720 | 17 | 1040 | 18 |
| 18 | S-TRT | 690 | 14 | 990 | 15 |
| 19 | S-TRT | 820 | 18 | 1210 | 20 |
| 20 | S-TRT | 960 | 20 | 1330 | 22 |
| 21 | S-TRT | 830 | 13 | 1270 | 13 |
| 22 | S-TRT | 790 | 21 | 1150 | 22 |
| 23 | S-TRT | 910 | 17 | 1260 | 17 |
| 24 | S-TRT | 830 | 24 | 1290 | 25 |
| 25 | Placebo | 720 | 22 | 710 | 77 |
| 26 | Placebo | 550 | 7 | 560 | 7 |
| 27 | Placebo | 810 | 11 | 790 | 11 |
| 28 | Placebo | 700 | 17 | 710 | 17 |
| 29 | Placebo | 910 | 15 | 910 | 15 |
| 30 | Placebo | 750 | 21 | 750 | 21 |

TABLE 3

| Subject | Treatment | Initial Free T (ng/dL) | Initial Estradiol (ng/dL) | 4-week Free T (ng/dL) | 4-week Estradiol (ng/dL) |
|---|---|---|---|---|---|
| 1 | S-TRT | 50 | 15 | 250 | 16 |
| 2 | S-TRT | 20 | 22 | 200 | 22 |
| 3 | S-TRT | 80 | 30 | 290 | 32 |
| 4 | S-TRT | 60 | 15 | 160 | 15 |
| 5 | S-TRT | 40 | 19 | 240 | 19 |
| 6 | S-TRT | 30 | 16 | 220 | 17 |
| 7 | S-TRT | 60 | 72 | 300 | 23 |
| 8 | S-TRT | 80 | 11 | 290 | 11 |
| 9 | S-TRT | 50 | 25 | 260 | 26 |
| 10 | S-TRT | 80 | 26 | 240 | 26 |
| 11 | S-TRT | 70 | 21 | 210 | 22 |
| 12 | S-TRT | 80 | 16 | 310 | 17 |
| 13 | S-TRT | 30 | 19 | 260 | 20 |
| 14 | S-TRT | 60 | 22 | 150 | 25 |
| 15 | S-TRT | 70 | 19 | 190 | 20 |
| 16 | Placebo | 60 | 13 | 70 | 13 |
| 17 | Placebo | 40 | 17 | 40 | 17 |
| 18 | Placebo | 60 | 12 | 60 | 12 |
| 19 | Placebo | 20 | 18 | 70 | 18 |
| 20 | Placebo | 60 | 20 | 70 | 20 |

Example 9

This is a prophetic example. Participants aged 60 years or more who are at risk for AD are recruited. Thirty male participants are split into a group of 24 experimental subjects and 6 control subjects. Twenty female participants are split into a group of 15 experimental subjects and 5 control subjects. The experimental group receives oral testosterone replacement therapy (O-TRT). The control group receives a placebo. One pellet produced as described in Example 5 is administered orally to the male experimental subjects four times per week for four weeks. One pellet produced as described in Example 7 is administered orally to the female experimental subjects four times per week for four weeks. One pellet containing magnesium stearate administered orally to the control subjects four times per week for four weeks. Serum levels of free testosterone and estradiol are measured before O-TRT is administered and at one-week intervals thereafter. Results for male participants and female participants are displayed in Table 4 and Table 5, respectively. For the experimental group after four weeks of TRT, free testosterone levels increased and estradiol levels generally are unaffected.

For the experimental group after ten years of O-TRT once per week, 94% of the experimental do not develop AD. Over the same period, in the placebo group, only 28% do not develop AD. Additionally, the longevity, life span, and health span of the experimental group is improved relative to the control group since the start of the study by 28%, 25%, and 43%, respectively. After death of any individuals in the study, the brain tissue of those subjects is analyzed. It is noted that the β-amyloid proteins in the experimental group is significantly less than for the placebo group.

TABLE 4

| Subject | Treatment | Initial Free T (ng/dL) | Initial Estradiol (ng/dL) | 4-week Free T (ng/dL) | 4-week Estradiol (ng/dL) |
|---|---|---|---|---|---|
| 1 | O-TRT | 860 | 12 | 1110 | 12 |
| 2 | O-TRT | 920 | 15 | 1280 | 17 |
| 3 | O-TRT | 890 | 30 | 930 | 31 |
| 4 | O-TRT | 970 | 9 | 960 | 11 |
| 5 | O-TRT | 740 | 13 | 1050 | 13 |
| 6 | O-TRT | 720 | 13 | 1350 | 14 |
| 7 | O-TRT | 770 | 23 | 1180 | 22 |
| 8 | O-TRT | 820 | 7 | 1290 | 8 |
| 9 | O-TRT | 920 | 15 | 1320 | 15 |
| 10 | O-TRT | 810 | 25 | 1060 | 28 |
| 11 | O-TRT | 750 | 31 | 1210 | 32 |
| 12 | O-TRT | 880 | 15 | 1180 | 17 |
| 13 | O-TRT | 980 | 13 | 1270 | 13 |
| 14 | O-TRT | 640 | 21 | 1030 | 23 |
| 15 | O-TRT | 700 | 16 | 1150 | 16 |
| 16 | O-TRT | 640 | 12 | 1050 | 14 |
| 17 | O-TRT | 730 | 18 | 1010 | 18 |
| 18 | O-TRT | 720 | 13 | 980 | 15 |
| 19 | O-TRT | 830 | 19 | 1220 | 20 |
| 20 | O-TRT | 960 | 19 | 1350 | 21 |
| 21 | O-TRT | 810 | 14 | 1220 | 15 |
| 22 | O-TRT | 770 | 20 | 1190 | 21 |
| 23 | O-TRT | 890 | 18 | 1220 | 18 |
| 24 | O-TRT | 810 | 23 | 1230 | 23 |
| 25 | Placebo | 720 | 23 | 710 | 23 |
| 26 | Placebo | 550 | 6 | 560 | 7 |
| 27 | Placebo | 810 | 12 | 790 | 12 |
| 28 | Placebo | 700 | 16 | 710 | 17 |
| 29 | Placebo | 910 | 16 | 910 | 17 |
| 30 | Placebo | 750 | 20 | 750 | 21 |

TABLE 5

| Subject | Treatment | Initial Free T (ng/dL) | Initial Estradiol (ng/dL) | 4-week Free T (ng/dL) | 4-week Estradiol (ng/dL) |
|---|---|---|---|---|---|
| 1 | O-TRT | 60 | 15 | 220 | 16 |
| 2 | O-TRT | 30 | 22 | 260 | 72 |
| 3 | O-TRT | 80 | 30 | 240 | 32 |
| 4 | O-TRT | 40 | 15 | 190 | 15 |
| 5 | O-TRT | 40 | 19 | 280 | 19 |
| 6 | O-TRT | 30 | 16 | 250 | 17 |
| 7 | O-TRT | 70 | 22 | 300 | 23 |
| 8 | O-TRT | 30 | 11 | 320 | 11 |
| 9 | O-TRT | 50 | 25 | 210 | 26 |
| 10 | O-TRT | 60 | 26 | 280 | 26 |
| 11 | O-TRT | 20 | 21 | 210 | 22 |
| 12 | O-TRT | 40 | 16 | 300 | 17 |
| 13 | O-TRT | 80 | 19 | 250 | 20 |
| 14 | O-TRT | 50 | 22 | 180 | 25 |
| 15 | O-TRT | 40 | 19 | 250 | 20 |
| 16 | Placebo | 60 | 13 | 70 | 13 |
| 17 | Placebo | 40 | 17 | 40 | 17 |
| 18 | Placebo | 60 | 12 | 60 | 12 |
| 19 | Placebo | 20 | 18 | 20 | 18 |
| 20 | Placebo | 60 | 20 | 70 | 20 |

Example 10

This is a prophetic example. The 40 and 42 amino acid forms are the most abundant B-amyloid (Aβ) peptide forms found in AD brain senile plaques, as disclosed herein. However, the number of senile plaques in a particular region of the AD brain correlates poorly with the local extent of neuron death or synaptic loss, or with cognitive impairment (Sisodia et al., 1990). Studies have shown a robust correlation between the soluble human Aβ 1-42 oligomer (AβO) levels and the extent of synaptic loss and severity of cognitive impairment (Sakono et al., 2010). This example investigates the neuroprotective effect of the composition prepared as described in Example 2 on cortical neurons incubated for 24 hours in the presence of AβO, an in vitro model of AD (Callizot et al., 2013). Brain-derived neurotrophic factor (BDNF) is used as a positive control in this study.

Cortical rat neurons are cultured at +37° C. in a humidified air/$CO_2$ (95/5) atmosphere. After 11 days of culture, cortical neurons are intoxicated with human AβO 1-42 at 10 μM for 24 hrs. Cultures are performed using the following conditions: (A) Medium without human AβO 1-42 (control) for 24 h; (B) Human AβO 1-42 (10 μM) for 24 h; (C) Human AβO 1-42 (10 μM) for 24 h with the composition of Example 2; and (D) Human AβO 1-42 (10 μM) for 24 h with BDNF (50 ng/ml).

The total number of cortical neurons that survive after 24 h incubation are counted to determine the end point evaluation. AβO applied at 10 μM for 24 h induces a large decrease (−40%) in cortical neurons. Application of reference compound BDNF (50 ng/ml) inhibits cell death resulting from AβO. These results validate the study. The composition of Example 2 reduces the toxic effect of AβO in a dose dependent manner, as shown in the following table. For example, the proportion of neuron survival is 87% of the medium control when incubated with the composition of Example 2 at 200 μg/ML.

| Concentration of testosterone composition (μg/mL) | 10 | 25 | 50 | 100 | 200 |
|---|---|---|---|---|---|
| Proportion of neuron survival in presence of AβO compared to the medium control | 71% | 74% | 77% | 79% | 87% |

Example 11

This is a prophetic example. In this study, the diagnosis of AD patients was consistent with the AD diagnostic criteria for "probable or possible AD" established by the National Institute of Neurological and Communicative Disorders and Stroke and the Alzheimer's disease and Related Disorders Association. In this study, a total of 20 AD patients, both male and female, are recruited as participants according the following criteria: (1) aged 65 to 85 years; (2) scores ranged from 10 to 24 points in Mini-Mental State Examination (MME); (3) hearing abilities to reliably complete the research evaluation; and (4) reliable caregivers to provide caregiver information and supervise the patients' accurate intake of the oral testosterone replacement therapy (O-TRT) described in Example 9. A total of eight non-AD patients, both male and female, are recruited as control participants. The inclusion criteria of the control participants is to be healthy and aged 65 to 85 years with normal overall cognitive function, no significant memory or other cognitive dysfunction, and a MME score greater than 24. The male participants received the O-TRT described in Example 5. The female participants received the O-TRT described in Example 7. The O-TRT was administered to the participants as follows: two pellets per day taken with food per 10 days for 30 days and then increased to four pellets per day taken with food per 10 days for 30 days for a period of six months. Results of the study after the six month O-TRT period are displayed in Table 6. The positive control showed an improvement, on average, of 4% on the MME score. Whereas the AD patients taking O-TRT showed an improvement of 30%. MRI scans showed the AD patients taking O-TRT had significantly increased brain function.

TABLE 6

| Subject | Treatment | Age | Gender | Initial MME score | Final MME score |
|---|---|---|---|---|---|
| 1 | O-TRT | 65 | M | 24 | 28 |
| 2 | O-TRT | 65 | F | 24 | 27 |
| 3 | O-TRT | 67 | M | 23 | 27 |
| 4 | O-TRT | 68 | M | 11 | 26 |
| 5 | O-TRT | 69 | F | 21 | 25 |
| 6 | O-TRT | 71 | M | 21 | 26 |
| 7 | O-TRT | 73 | M | 21 | 27 |
| 8 | O-TRT | 75 | F | 20 | 26 |
| 9 | O-TRT | 75 | M | 20 | 27 |
| 10 | O-TRT | 77 | F | 18 | 25 |
| 11 | O-TRT | 80 | F | 17 | 25 |
| 12 | O-TRT | 80 | M | 17 | 24 |
| 13 | O-TRT | 81 | F | 16 | 73 |
| 14 | O-TRT | 81 | F | 15 | 22 |
| 15 | O-TRT | 81 | M | 15 | 21 |
| 16 | O-TRT | 79 | F | 14 | 18 |
| 17 | O-TRT | 87 | M | 14 | 17 |
| 18 | O-TRT | 83 | F | 11 | 15 |
| 19 | O-TRT | 85 | F | 10 | 14 |
| 20 | O-TRT | 85 | M | 10 | 13 |
| 21 | Control | 65 | M | 29 | 29 |
| 77 | Control | 68 | F | 28 | 28 |
| 23 | Control | 72 | F | 27 | 28 |
| 24 | Control | 73 | M | 27 | 28 |
| 25 | Control | 80 | M | 26 | 27 |
| 26 | Control | 87 | F | 26 | 77 |
| 27 | Control | 79 | M | 25 | 27 |
| 28 | Control | 71 | F | 25 | 27 |

Example 12

This is a prophetic example. In this study, postmenopausal women (n=60) received a diagnosis of Alzheimer's disease from a neurologist or geriatrician. Control women without a diagnosis (n=60) also participated in the study. The study participants are split into a group of 60 experimental patients and 60 control patients. The mixed composition described in Example 2 is given transdermally to patients once a day for 10 days every 30 days over the course of the study. The control group received a placebo containing magnesium strearate. Cerebrospinal fluid (CSF) was collected and stored according to standardized local procedures. Neurofilament Light Chain (NfL) was measured in duplicates by the ELISA according to the manufacturer's instructions. CSF NfL levels were normalized by log transformation and compared between patients. CSF NfL levels were lower in patient who received the composition than in controls after 6 months.

Example 13

This is a prophetic example. In this study, a group of individuals that are at risk of developing AD are administered a composition as described in Example 2 with a MIND diet. A control group were administered a placebo and a MIND diet. The study participants were split into a group of 50 experimental patients and 50 control patients. The composition as described in Example 2 is given transdermally to patients once a day for 10 days every 30 days over the course of the study. Neurofilament Light Chain (NfL) was measured in duplicates by the ELISA according to the manufacturer's instructions. CSF NfL levels were normalized by log transformation and compared between patients. CSF NfL levels were lower in patient who received the composition than in controls after 6 months.

Example 14

This is a prophetic example. In this study, all mice are maintained in accordance with the NIH standards for all experimental protocols. Sixty male mice are selected for the study. Fifteen of the mice are native (native). Forty-five are transgenic mice designed to experience Alzheimer's-like symptoms within one year (APP23). Fifteen of the APP23 mice are used as controls (CONT), fifteen of the APP23 mice are periodically administered an aromatase inhibitor in a slow release pellet (EXPT-AI), and fifteen APP23 mice are periodically administered a slow release pellet composition including an aromatase inhibitor, testosterone and estriol (EXPT-TAIE). Levels of testosterone in the blood and in the brain decrease gradually with age in all male mice regardless of genotype. The levels of testosterone in the EXPT-AI and EXPT-TAIE groups is higher than the native or CONT group. The levels of testosterone in the EXPT-TAIE are higher than in the EXPT-AI group. At 1 year of age, all 15 of the CONT mice developed AD-like neuropathology as measured by the β-amyloid 42/β-amyloid 40 ratio and the extent of neuronal loss of the hippocampus. None of the native mice developed AD-like neuropathy. None of the EXPT-AI developed AD-like neuropathology after a period of 1 year. At 2 years of age, 6 of the EXPT-AI developed AD-like neuropathology. At 3 years of age, 11 of the EXPT-AI developed AD-like neuropathology. The EXPT-TAIE performed better with 0 mice developing AD-like neuropathology at 2 and 3 years of age.

What is claimed is:

1. A composition, comprising:
   about 1000 mg to about 5000 mg testosterone;
   about 5 mg to about 50 mg of an aromatase inhibitor; and
   about 10 mg to about 200 mg estriol,
   wherein the composition produces super-physiologically high levels of testosterone in a subject,
   wherein the composition is in a form for subcutaneous administration.

2. The composition of claim 1, further comprising a progesterone source.

3. The composition of claim 1, further comprising one or more glucocorticoids.

4. The composition of claim 1, wherein the aromatase inhibitor is selected from anastrozole, letrozole, exemestane, or combinations thereof.

5. The composition of claim 1, further comprising phytoestrogen.

6. The composition of claim 1, further vitamin D3.

7. The composition of claim 1, wherein the aromatase inhibitor is anastrozole, and wherein the testosterone and anastrozole are in ratio from about 50:1 to about 100:1.

8. The composition of claim 1, wherein the amount of testosterone to the aromatase inhibitor is in a ratio of from about 100:1.

9. The composition of claim 1, wherein the amount of testosterone to the aromatase inhibitor is in a ratio of from about 50:1.

10. The composition of claim 1, wherein the form for subcutaneous form is a pellet and the pellet has a mass from about 50 to 600 mg.

11. The composition of claim 1, wherein the amount of testosterone is from about 1500 mg to about 2500 mg testosterone.

12. The composition of claim 1, wherein the composition further comprises dexamethasone.

13. The composition of claim 1, wherein the composition further comprises an androgen.

14. The composition of claim 13, wherein the androgen is selected from dehydroepiandrosterone sulfate or androstenedione.

15. The composition of claim 3, wherein the one or more glucocorticoids is selected from the group consisting prednisone, prednisolone, dexamethasone, cortisone, methylprednisolone, betamethasone, triamcinolone, fludrocortisone acetate, deoxycorticosterone acetate, or a combination thereof.

16. The composition of claim 1, wherein the composition produces in the subject equal to or greater than 24 ng/dL free testosterone in a male or greater than or equal to 10 ng/dL free testosterone in a female.

17. The composition of claim 1, wherein the composition inhibits the conversion of testosterone to estradiol.

18. The composition of claim 1, wherein the composition upregulates neprilysin activity.

19. The composition of claim 1, wherein the composition reduces hyperphosphorylation of the tau protein.

20. A composition, comprising:
   about 1000 mg to about 5000 mg testosterone;
   about 5 mg to about 50 mg of an aromatase inhibitor;
   about 10 mg to about 200 mg estriol source;
   about 50 mg to about 400 mg of progesterone; and
   about 100 mg to about 1000 mg of hydrocortisone,
   wherein the composition is in a form for subcutaneous administration,
   wherein the composition produces super-physiologically high levels of testosterone in a subject.

* * * * *

UNITED STATES PATENT AND TRADEMARK OFFICE
CERTIFICATE OF CORRECTION

PATENT NO. : 12,083,130 B2
APPLICATION NO. : 17/255927
DATED : September 10, 2024
INVENTOR(S) : Arnold Edward Friedman et al.

Page 1 of 3

It is certified that error appears in the above-identified patent and that said Letters Patent is hereby corrected as shown below:

On the Title Page

On Page 3, Column 1, Line 18, under item (56) Other Publications, delete "Neutrol," and insert --Neurol,--.

On Page 3, Column 1, Line 44, under item (56) Other Publications, delete "Fibrosi"" and insert --Fibrosis"--.

On Page 3, Column 2, Line 63, under item (56) Other Publications, delete "Memor," and insert --Memory,--.

In the Specification

In Column 2, Line 20, delete "1.0-99.5%" and insert --10-99.5%--.

In Column 4, Line 19, delete "anatrozole," and insert --anastrozole,--.

In Column 6, Line 50, delete "p-toluensulfonic," and insert --p-toluenesulfonic,--.

In Column 7, Line 54, delete "'including,"containing,'" and insert --'including,' 'containing,'--.

In Column 7, Line 61, delete "preferred," and insert --'preferred,'--.

In Column 13, Line 29, delete "proprionate," and insert --propionate,--.

In Column 13, Lines 29-30, delete "endecanoate," and insert --undecanoate,--.

In Column 14, Line 7, delete "aminogluthetimide," and insert --aminoglutethimide,--.

Signed and Sealed this
Tenth Day of December, 2024

Katherine Kelly Vidal
*Director of the United States Patent and Trademark Office*

CERTIFICATE OF CORRECTION (continued)
U.S. Pat. No. 12,083,130 B2

In Column 14, Line 9, delete "androstatrien" and insert --androstatriene--.

In Column 20, Line 27, delete "40%." and insert --40%,--.

In Column 23, Lines 45-46, delete "10%-70%, 10%-70%," and insert --10%-70%,--.

In Column 24, Line 33, delete "zaleplon," and insert --zaleplon;--.

In Column 26, Line 12, delete "salt," and insert --salt;--.

In Column 26, Line 26, delete "daily, in" and insert --daily. In--.

In Column 27, Line 31, delete "ore" and insert --or--.

In Column 28, Lines 27-28, delete "trimethyammonium," and insert --trimethylammonium,--.

In Column 29, Line 35, delete "ultramylopectin," and insert --ultraamylopectin,--.

In Column 29, Line 61, delete "providone" and insert --povidone--.

In Column 29, Line 64, delete "doses" and insert --doses.--.

In Column 32, Line 42 (Approx.), delete "amyvid-PET" and insert --amyloid-PET--.

In Columns 33-34, Line 10, (TABLE 1-continued), delete "Nov. 9, 2015" and insert --Nov. 19, 2015--.

In Columns 33-34, Line 23, (TABLE 1-continued), delete "24E," and insert --24F,--.

In Columns 33-34, Line 25, (TABLE 1-continued), delete "7600" and insert --2600--.

In Columns 33-34, Line 36, (TABLE 1-continued), delete "RC" and insert --HC--.

In Columns 33-34, Line 37, (TABLE 1-continued), delete "RC" and insert --HC--.

In Columns 33-34, Line 39, (TABLE 1-continued), delete "37" and insert --32--.

In Columns 33-34, Line 40, (TABLE 1-continued), delete "37" and insert --32--.

In Columns 33-34, Line 42, (TABLE 1-continued), delete "7640" and insert --2640--.

In Columns 33-34, Line 46, (TABLE 1-continued), delete "7600" and insert --2600--.

In Column 33, Line 48 (Approx.), delete "LISP" and insert --USP--.

CERTIFICATE OF CORRECTION (continued)
U.S. Pat. No. 12,083,130 B2

In Column 35, Line 18 (Approx.), delete "composition)." and insert --composition),--.

In Column 36, Line 28 (Approx.), delete "77" and insert --22--.

In Column 36, Line 37 (Approx.), delete "77" and insert --22--.

In Column 36, Line 64 (Approx.), delete "70" and insert --20--.

In Column 38, Line 7 (Approx.), delete "72" and insert --22--.

In Column 39, Line 49 (Approx.), delete "11" and insert --22--.

In Column 39, Line 57 (Approx.), delete "73" and insert --23--.

In Column 39, Line 64 (Approx.), delete "77" and insert --22--.

In Column 40, Line 5, delete "77" and insert --27--.

In Column 40, Line 21, delete "strearate." and insert --stearate.--

In the Claims

In Column 42, Claim 20, Line 31 (Approx.), delete "estriol source;" and insert --estriol;--.